United States Patent [19]

Bourgery et al.

[11] 4,413,001

[45] Nov. 1, 1983

[54] N-ARYL OXAZOLIDINONES, OXAZOLIDINETHIONES, PYRROLIDINONES, PYRROLIDINES AND THIAZOLIDINONES

[75] Inventors: Guy R. Bourgery, Colombes; Colette A. Douzon, Paris; Jean-Francois R. Ancher, Rueil-Malmaison; Alain P. Lacour, La Varenne; Patrick G. Guerret, Rueil-Malmaison; Michel Langlois, Buc; Philippe L. Dostert, Le Vesinet, all of France

[73] Assignee: Delalande S.A., Courbevoie, France

[21] Appl. No.: 388,867

[22] Filed: Jun. 16, 1982

Related U.S. Application Data

[62] Division of Ser. No. 45,143, Jun. 4, 1979, Pat. No. 4,348,393.

[30] Foreign Application Priority Data

Jun. 9, 1978 [FR] France .............................. 78 17388
Aug. 17, 1978 [FR] France .............................. 78 24024

[51] Int. Cl.³ .................... A61K 31/42; A61K 31/44; C07D 263/14; C07D 263/46

[52] U.S. Cl. ................................. 424/272; 546/275; 548/229; 424/263

[58] Field of Search ....................... 548/229; 546/275; 424/272, 263

[56] References Cited

U.S. PATENT DOCUMENTS

| | | | |
|---|---|---|---|
| 3,641,036 | 2/1972 | Fauran et al. | 424/272 |
| 3,654,298 | 4/1972 | Douzon et al. | 424/272 |
| 4,150,029 | 4/1979 | Dostert et al. | 424/272 |
| 4,250,318 | 2/1981 | Dostert et al. | 548/229 |

FOREIGN PATENT DOCUMENTS

| | | | |
|---|---|---|---|
| 2380780 | 10/1978 | France | 424/272 |
| 2381037 | 10/1978 | France | 424/272 |
| 2076813 | 12/1981 | United Kingdom | 424/272 |

*Primary Examiner*—Donald G. Daus
*Assistant Examiner*—S. A. Gibson
*Attorney, Agent, or Firm*—Flynn, Thiel, Boutell & Tanis

[57] ABSTRACT

N-aryl oxazolidinones, oxazolidinethiones, pyrrolidinones, pyrrolidines and thiazolidinones are disclosed. These compounds possess antidepressant activity.

7 Claims, No Drawings

N-ARYL OXAZOLIDINONES, OXAZOLIDINETHIONES, PYRROLIDINONES, PYRROLIDINES AND THIAZOLIDINONES

This is a division, of application Ser. No. 45,143, filed June 4, 1979 now U.S. Pat. No. 4,348,393.

The present invention relates to N-aryl-oxazolidinones, oxazolidinethiones, pyrrolidinones, pyrrolidines and thiazolidinones, their process of preparation and their therapeutic application.

The compounds of the invention have the formula:

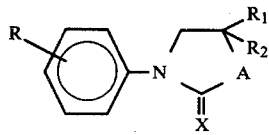

in which the parameters (X, A, $R_1$) take anyone of the following values: (a) (O,O,H), $R_2$ is:

either an ester group of formula $-CH_2-OCOR_3$ in which $R_3$ is a linear or branched alkyl moiety having from 1 to 8 carbon atoms, a cyclohexyl group, a phenyl nucleus, a methoxymethyl or a phenyloxymethyl group; and R is in para position and is anyone of the following groups: n-butyloxy, methyl-3 butyloxy, cyclopentylmethoxy, cyclohexylmethoxy, cyano-2 ethoxy, cyanomethoxy, benzyloxy of formula

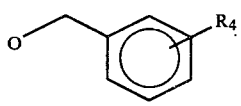

in which $R_4$ is a hydrogen or a chlorine atom in meta position, a fluorine atom in meta or para position, or a cyano or nitro group in meta position; disubstituted para-benzyloxy group of formula

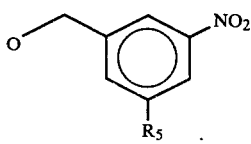

in which $R_5$ is a chlorine atom or a cyano group;

or an ether group of formula $-CH_2-OR_6$ in which $R_6$ is a linear or branched alkyl group having from 1 to 5 carbon atoms, a cyclohexyl, allyl, propargyl or methoxymethyl group; and R is the methyl group in meta position, or is anyone of the following groups located in para position:
linear or branched alkyloxy having from 4 to 6 carbon atoms,
cycloalkylmethyloxy the cycloalkyl moiety of which has from 4 to 7 carbon atoms,
(methyl-1 cyclopentyl-1)methyloxy,
(cyclopentene-1 yl ) methyloxy,
(cyclohexene-1 yl ) methyloxy,
(butene-2) oxy,
(methyl-3 butene-2) oxy,
chloro-4 butyloxy,
cyano-2 ethoxy; cyano-3 propoxy or cyano-4 butoxy,
oxo-2 propoxy,
(oxo-4 cyclohexyl-1) methyoxy,
morpholino-2 ethoxy,
N,N dimethyl amino,
(tetrahydropyranyl-4) methoxy or (tetra hydropyranyl-3) methoxy,
benzyloxy of formula

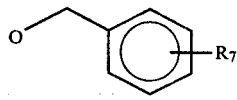

in which $R_7$ is selected from the group consisting of: H, 3—Cl, 4—Cl, 3—F, 4—F, 3—I, 3—Br, 3—$CF_3$, 3—$NO_2$, 4—$NO_2$, 4—CN, 3-cyanobenzyloxy, the corresponding compound of formula (I) having an asymmetric carbon being isolated as a racemic mixture or as two enantiomers or formulae (Ia) and (Ib) having respectively the absolute configuration: R(—) and S(+)

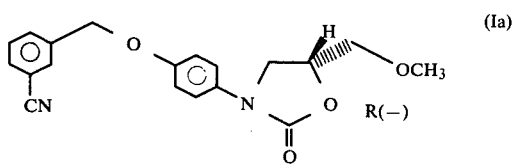

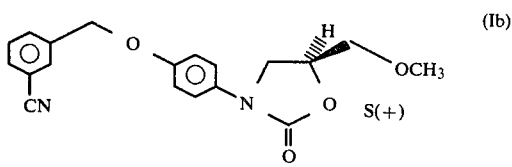

disubstituted benzyloxy of formula

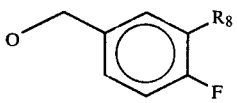

in which $R_8$ is a chlorine atom, or a cyano or nitro group;
disubstituted benzyloxy of formula

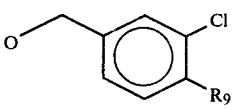

in which $R_9$ is a chlorine atom or a nitro group;
disubstituted benzyloxy of formula

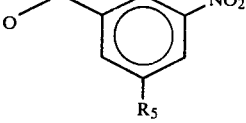

in which $R_5$ is a chlorine atom or a cyano group;
3,5-dichlorobenzyloxy;
substituted or non substituted styryl chain of trans configuration and of formula

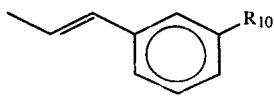

in which R$_{10}$ is a hydrogen or chlorine atom, or a cyano or nitro group;
substituted or non substituted styryl chain of cis configuration and of formula

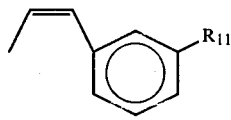

in which R$_{11}$ is a hydrogen atom or a nitro group,

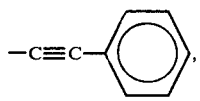

or phenethyl chain, or
phenyl nucleus;
or an amine group of formula

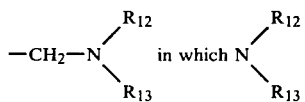

is selected from the group consisting of:

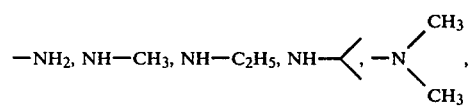

and R is in para position and is selected from the group consisting of:
n-butyloxy, methyl-3 butyloxy, cyclopentylmethoxy, cyclohexylmethoxy, cyanomethoxy or cyano-2 ethoxy group;
benzyloxy group of formula

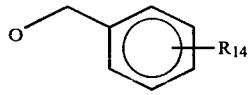

in which R$_{14}$ has one of the following values: H, 3—Cl, 4—F, 3—CN, 3—NO$_2$; or
disubstituted benzyloxy group of formula

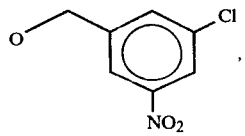

(b) (O,CH$_2$,H), R$_2$ is the hydroxymethyl group, and R is the para-(metanitro) benzyloxy group;
(c) (H$_2$,CH$_2$,H), R$_2$ is the hydroxymethyl group and R is the parabenzyloxy group;
(d) (O,S,H), R$_2$ is the methoxymethyl group and R is the para-(metanitro) benzyloxy group;
(e) (S,O,H), R$_2$ is:
either a hydroxymethyl group and R in para position is selected from the group consisting of:
a linear or branched alkyloxy group having from 2 to 5 carbon atoms,
a cyclopentylmethoxy, cyclohexylmethoxy, (cyclohexene-1 yl) methoxy or (tetrahydropyranyl-4) methoxy group,
a cyanomethoxy, cyano-2 ethoxy, cyano-3 propoxy or cyano-4 butoxy group,
a benzyloxy group of formula

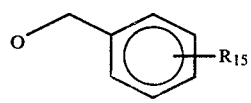

in which R$_{15}$ has one of the following values: 3—Cl, 4—Cl, 3—F, 4—F, 3—NO$_2$, 3—CN, 3—CF$_3$, or
a disubstituted benzyloxy group of formula:

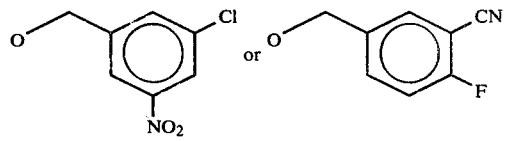

or an ether group of formula —CH$_2$—O—R$_{16}$ in which R$_{16}$ is a linear or branched alkyl group having from 1 to 3 carbon atoms, and R in para position is selected from the group consisting of:
methyl-3 n-butyloxy, cyclopentylmethoxy, cyclohexylmethoxy or cyano-4 butoxy group),
a benzyloxy group of formula

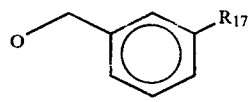

in which R$_{17}$ is a cyano or nitro group
the cyano-3 nitro-5 benzyloxy group, or
the pyridinyl-3 methoxy group,
or an ester group of formula —CH$_2$—OCOR$_{18}$ in which R$_{18}$ is a methyl or ethyl group and R in para position is the cyclohexylmethoxy gru or a benzyloxy group of formula

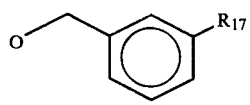

in which $R_{17}$ is a cyano or nitro group.

(A) The process for preparing the compounds of formula (I) in which the parameters $(X,A,R_1,R_2)$ represent $(O,O,H, CH_2OCOR_3)$, $R_3$ having the same meanings as above, consists in condensing the compounds of formula:

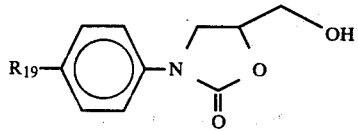
(II)

in which $R_{19}$ represents one of the following groups: n-butyloxy; methyl-3 butoxy; cyclopentylmethoxy; cyclohexylmethoxy; cyano-2 ethoxy; cyanomethoxy; benzyloxy of formula

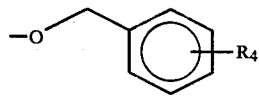

with $R_4$=H, 3—Cl, 3—F, 4—F, 3—CN or 3—$NO_2$; and benzyloxy of formula

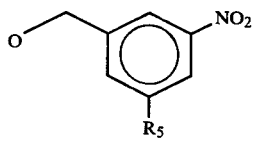

with $R_5$=Cl or CN, with the acid chlorides of formula:

 $R_3COCl$ (III)

in which $R_3$ has the same meanings as above.

This condensation is carried out preferably at room temperature, either in an organic solvent such as chloroform or tetrahydrofuran in the presence of triethylamine, or in pyridine.

The compounds of formula (II), except those in which $R_{19}$ is the cyano-2 ethoxy group, are prepared according to the method described in Belgian Pat. No. 851 893 (reacting the p-hydroxyphenyl-3 hydroxymethyl-5 oxazolidinone-2 on the suitable chloride, bromide or tosylate).

The compounds of formula (II) in which $R_{19}$ is the cyano-2 ethoxy group is obtained by cyclising, by action of ethyl carbonate, the compound of formula

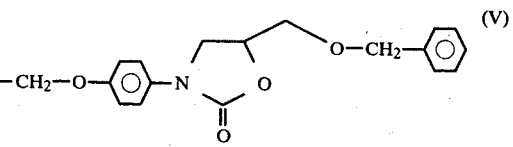
(IV)

to obtain the compound of formula:

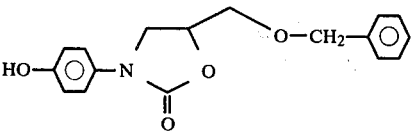
(V)

which is selectively hydrogenolysed in the presence of palladium on charcoal, in ethanol, preferably at room temperature to give the compound of formula:

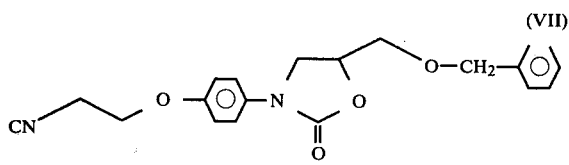
(VI)

which is condensed with acrylonitrile in the presence of triton B, to give the compound of formula:

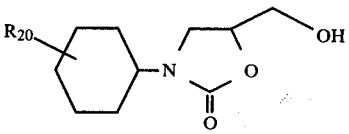
(VII)

which is then hydrogenolysed in ethanol in the presence of palladium on charcoal, and preferably, of some drops of hydrochloric ethanol.

The compound of formula (IV) is obtained in condensing, in methanol or ethanol, the parabenzyloxyaniline with the benzyloxy-3 epoxy-1,2 propane.

(B) The process for preparing the compounds of formula (I) in which the parameters $(X,A,R_1)$ represents $(O,O,H)$, and $R_2$ is an ether group of formula —$CH_2$—$OR_6$ in which $R_6$ has the same meanings as above consists:

(1) either in submitting the compounds of formula:

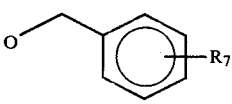
(IIa)

in which $R_{20}$ represents the meta-methyl group or one of the following groups in para position: linear or branched alkyloxy having from 4 to 6 carbon atoms; cycloalkylmethoxy the alkyl moiety of which has from 4 to 7 carbon atoms; (methyl-1 cylcopentyl-1) methoxy; butene-2 oxy; methyl-3 butene-2 oxy; (cyclopentene-1 yl) methoxy; (cyclohexene-1 yl) methoxy; morpholino-2 ethoxy; chloro-4 butyloxy; (oxo-4 cylcohexyl-1) methoxy; oxo-2 propoxy; cyano-3 propoxy; cyano-2 ethoxy; cyano-4 butoxy; dimethyl amino; (tetrahydropyranyl-4) methoxy; (tetrahydropyranyl-3) methoxy;

benzyloxy of formula in which $R_7$=H, 3—Cl, 4—Cl, 3—F, 4—F, 3—I, 3—Br, 3—CF$_3$, 3—NO$_2$, 4—NO$_2$, 3—CN, 4—CN; disubstituted benzyloxy of formula:

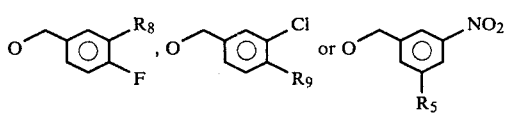

in which $R_8$, $R_9$ and $R_5$ have the same meanings as above; and

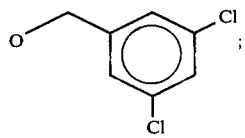

to a so-called "phase transfer" reaction, in the presence of a catalyst so-called "phase transfer catalyst", and in a basic medium with derivatives of formulae:

(CH$_3$)$_2$ SO$_4$
$R_6$—Cl or
$R_6$—I in which $R_6$ has the same meanings as previously.

The used catalyst is preferably the benzyltributylammonium bromide, but it can be chosen among the catalysts mentioned in the following documents: —Synthesis 1973, 441, and Angewandte Chemie, Edit. Int. Vol. 13, 170, (1974).

The used base is preferably aqueous soda and the reaction can be carried out in an organic solvent such as methylene chloride or benzene.

The compounds of formula (IIa), except those in which $R_{20}$ represents the cyano-2 ethoxy group which is obtained by hydrogenolysing the compound of formula (VII), are prepared according to the method described in Belgian Pat. No. 851 893.

(2) or in condensing the compounds of formula:

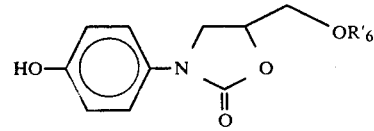

in which $R'_6$ is a linear or branched alkyl group having from 'to 5 carbon atoms, a cylcohexyl or a methoxymethyl group, with the chlorides or tosylates of formula:

$R'_{20}$—Cl
$R'_{20}$—OTs in which $R'_{20}$ has the same meanings as $R_{20}$ except for the meta-methyl and paracyano-2 ethoxy groups.

The condensation is carried out with reflux in acetone or acetonitrile in the presence of potassium carbonate, or with reflux in dimethylformamide in the presence of sodium hydride.

The compounds of formula (VIII) are obtained by hydrogenolysing in the presence of palladium on charcoal, the compounds of formula:

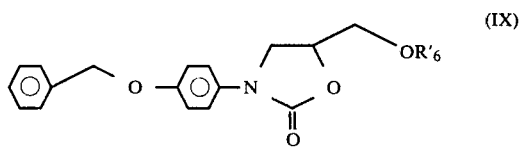

in which $R'_6$ has the same meanings as in formula (VIII).

The compounds of formula (IX) are obtained by a three stage synthesis which consists in condensing the chlorhydrine of formula:

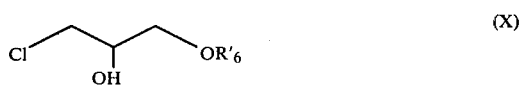

in which $R'_6$ has same meanings as in formula (IX) with phosgene, then in condensing product thus obtained with parabenzyloxyaniline and at last in cyclising the obtained product by means of ethanolic potash or sodium methylate in methanolic solution.

(3) or, when R is the cyano-2 ethoxy group, in reacting acrylonitrile in the presence of triton B with the compound of formula (VIII);

(4) or, according to the process described above for the synthesis of compounds of formula (IX), but with chlorohydrines of formula (X) and anilines of formula:

in which $R_{21}$ represents a trans styryl group of formula

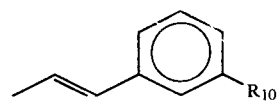

with $R_{10}$=H, Cl, CN, NO$_2$; a cis styryl group of formula

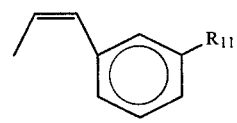

with $R_{11}$=H, NO$_2$; a stylbene group

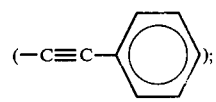

a phenethyl group; or a phenyl group; instead of the parabenzyloxyanoline;

(5) or, when (I) is (Ia) in submitting to a "phase transfer" reaction the compound of absolute configuration R(—) and having the formula:

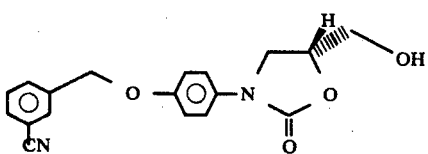 (IIb)

in presence of a phase transfer catalyst, of (CH$_3$)$_2$SO$_4$ and in a basic medium.

The compound of formula (IIb) is obtained by reacting the metacyanobenzyl chloride with the compound of formula:

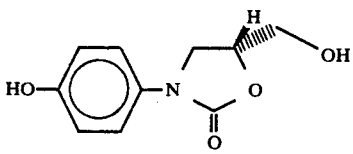 (IIc)

which is obtained by hydrogenolysing in the presence of palladium on charcoal, the compound of absolute configuration R(−) and having the formula:

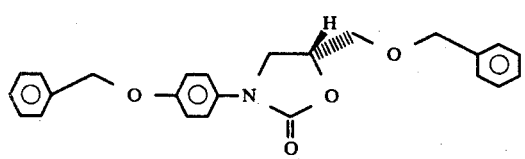 (Va)

This last compound is obtained according to the method described for the synthesis of compounds of formula (IX) but from parabenzyloxyaniline and benzyloxy-3 paratosyloxy-1 propanol-2 having the S(+) configuration, instead of the compound of formula (X).

(6) or, when (I) is (Ib), according to the process described for the synthesis of the compounds of formula (IX), but by using p-(cyano-3) benzyloxyaniline instead of parabenzyloxyaniline and methocy-3 paratosyloxy-1 propanol-2 of absolute configuration R and of formula:

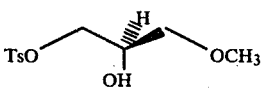 (XII)

instead of the compound of formula (X).

The compound of formula (XII) is obtained by reacting the tosyl chloride, in a benzene medium and in the presence of pyridine, with the methoxy-3 propane diol-1,2 of absolute configuration S and of formula:

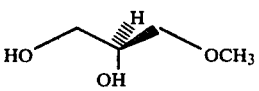 (XIII)

This compound of formula (XIII) is obtained by catalytically debenzylating, in the presence of palladium on charcoal, the compound of absolute configuration R and of formula:

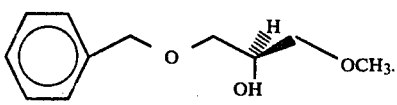 (XIV)

The compound of formula (XIV) is obtained by opening, with methanol in the presence of boron trifluoride etherate, benzyloxy-1 epoxy-2,3 propane having the absolute configuration S(+) and described in J. Chem. Soc. 1967 1021.

(C) The process for preparing the compounds of formula (I) in which the parameters (X,A,R$_1$) represent (O,O,H), R$_2$ represents an amine group of formula

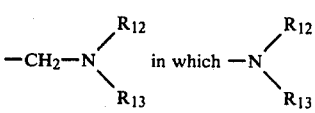

has the same meanings as above, consists in reacting amines of formula

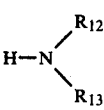

with the compounds of formula:

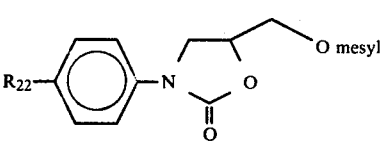 (XV)

in which R$_{22}$ is a n-butyloxy, methyl-3 butyloxy, cyclopentylmethoxy, cyclohexylmethoxy, cyanomethoxy, cyanoethoxy group, benzyloxy group of formula

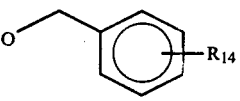

in which R$_{14}$ has the same meaning as above or a chloro-3-nitro-5 benzyloxy group.

The compounds of formula (XV) are obtained by action of mesyl chloride on the compounds of formula:

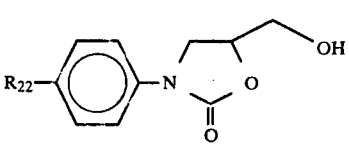 (IId)

in which R$_{22}$ has the same meanings as in formula (XV), the compounds of formula (IId) being obtained according to the process described in Belgian pat. No. 851 893.

(D) The process for preparing the compounds of formula (I) in which the parameters (X, A, R$_1$) represent (O,CH$_2$,H), R$_2$ represents the hydroxymethyl group and R represents the para(metanitro) benzyloxy group consists in reacting metanitrobenzyl chloride on the compound of formula:

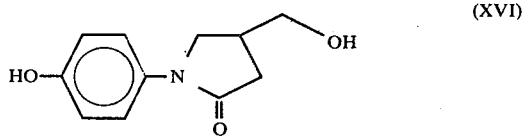
(XVI)

obtained by hydrogenolysing in the presence of palladium on charcoal, the compound of formula:

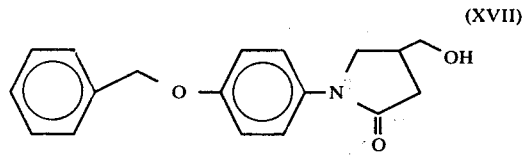
(XVII)

obtained by reducing with lithium borohydride the compound of formula:

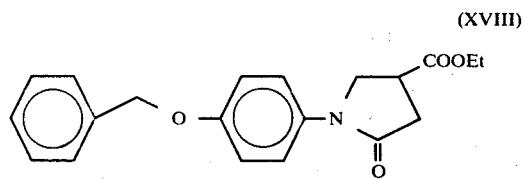
(XVIII)

The compound of formula (XVIII) is obtained by esterifying with ethanol in the presence of sulfuric acid, the compound of formula:

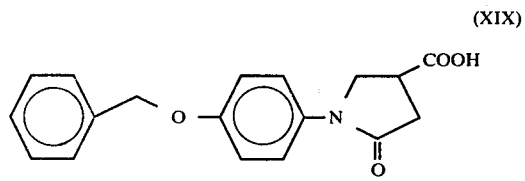
(XIX)

which is obtained by condensing parabenzyloxyaniline with itaconic acid.

The process for preparing the compound of formula (I) in which $(X,A,R_1)$ is $(H_2, CH_2,H)$, $R_2$ is the hydroxymethyl group and R is the parabenzyloxy group consists in reducing with lithium aluminium hydride the compound of formula (XVIII).

(E) The process for preparing the compound of formula (I) in which $(X, A, R_1)$ is $(O,S,H)$, $R_2$ is the methoxymethyl group and R is the para(metanitro) benzyloxy group consists in cyclising with phosgene the compound of formula:

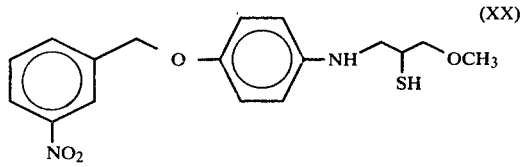
(XX)

obtained by condensing para(metanitro)benzyloxyaniline with methoxy methyl-2 thioxirane.

(F) The process for preparing the compounds of formula (I) in which the parameters $(X,A,R_1)$ are $(S,O,H)$, $R_2$ is a hydroxymethyl group or a $—CH_2OR_{16}$ group in which $R_{16}$ has the same meanings as above, consists in cyclising with thiophosgene, either compounds of formula:

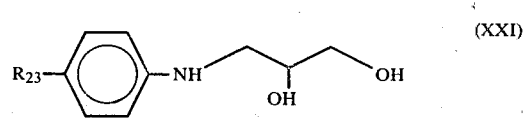
(XXI)

in which $R_{23}$ represents a linear or branched alkyloxy group having from 2 to 5 carbon atoms, cyclopentylmethoxy, cyclohexylmethoxy, (cyclohexane-1 yl) methoxy, (tetrahydropyrannl-4)methoxy, cyanomethoxy, cyano-2 ethoxy, cyano-3 propoxy, cyano-4 butoxy group, benzyloxy group of formula

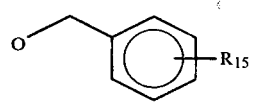

with $R_{15}=$3—Cl, 4-Cl, 3—F, 4—F, 3—NO$_2$, 3—CN or C—CF$_3$, (chloro-3 cyano-5) benzyloxy or (cyano-3 fluoro-4) benzyloxy group, — or compounds of formula:

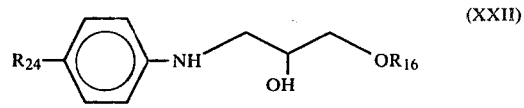
(XXII)

in which $R_{16}$ has the same meaings as above and $R_{24}$ represents a methyl-3 butoxy; cyclopentylmethoxy, cyclohexylmethoxy, cyano-4 butoxy group, a benzyloxy group of formula

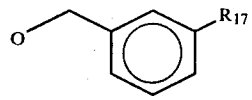

with $R_{17}=$CH or NO$_2$, a (cyano-3 nitro-5) benzyloxy or (pyrindinyl-3) methoxy group.

The compounds of formula (XXI) are obtained by condensing glycidol and anilines of formula:

(XIa)

in which $R_{23}$ has the same meanings as in formula (XXI), and the compounds of formula (XXII) are obtained by condensing anilines of formula:

(XIb)

in which $R_{24}$ has the same meanings as in formula (XXII) with the chlorohydrines of formula:

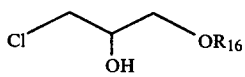 (Xa)

in which $R_{16}$ has the same meaning as above.

(G) The process for preparing the compounds of formula (I) in which the parameters $(X,A,R_1)$ represent $(S,O,H)$ and $R_2$ is an ester group of formula $R_{18}COOCH_2$ in which $R_{18}$ has the same meaning as above, consists in condensing the acid chloride of formula:

$R_{18}COCl$ (IIIa)

in which $R_{18}$ is as above, with the compounds of formula (I) having the following structure:

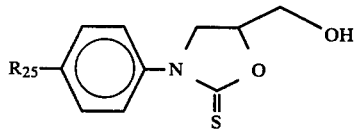 (Ic)

in which $R_{25}$ represents a cyclohexylmethoxy group or a benzyloxy group of formula

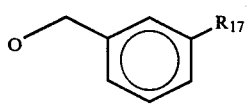

with $R_{17}$=CN or $NO_2$, according to the process described under chapter (A) above. The compounds (Ic) are obtained according to the process described under chapter (F) above.

The following preparations are given by way of example to illustrate the invention.

EXAMPLE I

Para (meta-nitrobenzyloxy) phenyl-3 acetoxy-methyl-5 oxazolidinone-2 [I]

Code number: 36.

A solution of 10.5 g of para(metanitrobenzyloxy)phenyl-3 hydroxy methyl-5 oxazolidinone-2 [(II), mp=135° C.], 2.5 cm³ of acetyl chloride and 4.5 cm³ of triethylamine in 100 cm³ of chloroform was left for 12 hours at room temperature. Then, the solution was diluted in water, the chloroformic phase was decanted, the solvent was evaporated and the residue was recrystallized in pure alcohol. 8 g of product were obtained.

| Yield: | 72% |
| Melting point: | 126° C. |
| Empirical formula: | $C_{19}H_{18}N_2O_7$ |
| Molecular weight: | 386.35 |
| Elementary analysis: | | | |

| | C | H | N |
| --- | --- | --- | --- |
| Calculated (%) | 59.06 | 4.70 | 7.25 |
| Found (%) | 59.10 | 4.56 | 6.95 |

With the same method, but from the corresponding reagents, the compounds of formula (I) were prepared, given in table I and bearing code numbers: 1 to 44; 103 to 108; 115, 117, 120 to 141; 178 and 208.

EXAMPLE 2

(paracyano-2 ethoxyphenyl)-3 hydroxymethyl-5 oxazolidinone-2 [II]

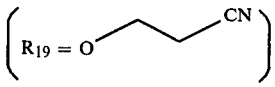

First Step: (p-benzyloxyphenyl)-3 benzyloxymethyl-5 oxazolidinone-2 [V]

This compound was obtained following a method in which a mixture of 0.2 mole of the compound of formula:

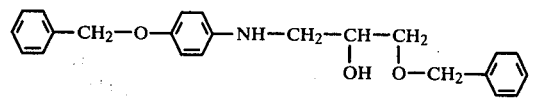

200 ml of ethyl carbonate and 8 ml of triethylamine is heated at 100°–110° C. for 5 hours, then the product was filtered and recrystallized in pure alcohol.

| Yield: | 80% |
| Melting point: | 126° C. |
| Empirical formula: | $C_{24}H_{23}NO_4$ |
| Molecular weight: | 389.43 |
| Elementary analysis: | | | |

| | C | H | N |
| --- | --- | --- | --- |
| Calculated (%) | 74.02 | 5.95 | 3.60 |
| Found (%) | 73.87 | 6.14 | 3.89 |

Second step: (p-hydroxyphenyl)-3 benzyloxymethyl-5 oxazolidinone-2 (VI)

A suspension of 18 g (0.046 mole) of the compound obtained in the first step and 2 g of 10% palladium charcoal in 400 ml of pure alcohol was hydrogenolysed in autoclave, at room temperature and under a hydrogen pressure of 4–5 kg. Then the mixture was filtered, the solvent evaporated and the residue recrystallized in pure alcohol.

| Yield: | 73% |
| Melting point: | 153° C. |
| Empirical formula: | $C_{17}H_{17}NO_4$ |
| Elementary analysis: | | | |

| | C | H | N |
| --- | --- | --- | --- |
| Calculated (%) | 68.21 | 5.73 | 4.68 |
| Found (%) | 68.38 | 5.62 | 4.46 |

By the same process, but from the corresponding reagents, the compound of formula (IIc) [mp=188° C., Empirical formula: $C_{10}H_{11}NO_4$] (from compound of formula (Va)); and the compound of formula (XVI) [mp=196° C., empirical formula: $C_{11}H_{13}NO_3$] (from compound of formula (XVII)) were obtained.

Third step: (p-cyanoethoxy-2-phenyl)-3-benzyloxymethyl-5 oxazolidinone-2 (VII)

A solution of 13 g (0.03 mole) of the compound prepared in the second step, in 45 g (0.86 mole) of acrylonitrile in the presence of 1 ml of triton B (40% in methanol), was brought to reflux for 15 hours. Then the acrylonitrile in excess was evaporated, the residue was taken up in 100 ml of N soda and filtered, the precipitate was washed with water then with ether and recrystallized in methanol.

| Yield | 60% |
| --- | --- |
| Melting point: | 112° C. |
| Empirical formula: | $C_{20}H_{20}N_2O_4$ |
| Elementary analysis: | |

| | C | H | N |
| --- | --- | --- | --- |
| Calculated (%) | 68.17 | 5.72 | 7.95 |
| Found (%) | 67.89 | 5.66 | 8.21 |

By the same method, but from the corresponding reagents, the compounds of formula (I) were prepared, given in table (I) and bearing code numbers 52 to 54 and 145 to 147.

Fourth step: (p-cyano-2 ethoxyphenyl)-3 hydroxymethyl-5 oxazolidinone-2 (II)

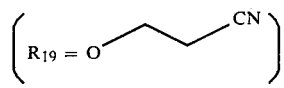

A suspension of 3.5 g (0.01 mole) of (p-cyano-2 ethoxyphenyl)-3 benzyloxymethyl-5 oxazolidinone-2, obtained in the preceding step, 0.4 g of 10% palladium charcoal and 0.05 ml of 7.5 N chlorhydric ethanol in 250 ml of dioxane, was hydrogenolysed in an autoclave, at a pressure of 1 kg of hydrogen and at room temperature. The mixture was filtered, the residue was purified by chromatography on a silica column. Eluted with the mixture chloroform-acetone 50/50, the product was obtained which was recrystallized in pure alcohol. Weight: 1 g.

| Yield: | 39% |
| --- | --- |
| Melting point: | 131° C. |
| Empirical formula: | $C_{13}H_{14}N_2O_4$ |
| Elementary analysis: | |

| | C | H | N |
| --- | --- | --- | --- |
| Calculated (%) | 59.53 | 5.38 | 10.68 |
| Found (%) | 59.06 | 5.24 | 10.37 |

EXAMPLE 3 para (meta-nitrobenzyloxy) phenyl-3 methoxymethyl-5 oxazolidinone-2 (I)

Code number: 61.

A mixture of 10.3 g of para (metanitrobenzyloxy) phenyl-3 hydroxymethyl- 5 oxazolidinone (IIa), 10.7 g of benzyltributylammonium bromide, 14.2 g of methyl iodide and 1.8 g of NaOH in 200 ml of water and 280 ml of methylene chloride, was brought to reflux for 50 hours. Then the mixture was decanted, the organic layer washed with water, the solvent evaporated, the residue taken up in ethyl acetate, the filtrate was filtered and chromatographied on a silica column; eluted with chloroform, 6.9 g of the product was obtained which was recrystallized in isopropanol.

| Yield: | 62% |
| --- | --- |
| Melting point: | 78° C. |

| Empirical formula: | $C_{18}H_{18}N_2O_6$ |
| --- | --- |
| Molecular weight: | 358.34 |
| Elementary analysis: | |

| | C | H | N |
| --- | --- | --- | --- |
| Calculated (%) | 60.33 | 5.06 | 7.82 |
| Found (%) | 60.52 | 5.10 | 7.92 |

By the same method, but from the corresponding reagents, the compounds of formula (I) were prepared, given in table (I) and bearing code numbers 45, 46, 55 to 57; 59, 64 to 73; 109 to 112; 142 to 156; 159 to 169; 179 to 186; 188, 197, 198 and 199 (Ia).

EXAMPLE 4 para-n-butyloxy phenyl-3 isopropyloxymethyl-5 oxazolidinone-2 (I)

Code number: 47

First step: para benzyloxyphenyl-3 isopropyl oxymethyl-5 oxazolidinone:2 (IX)

Code number: 225.

To a solution of 59 g of phosgene in 560 ml of dichloroethane was added 83.4 g of chloro-1 isopropyloxy-3 propanol-2 (X), then in 30 minutes a solution of 81.9 g of N, N-diethylaniline in 160 ml of dichloroethane. The mixture was heated to 50° C. for 2 hours, 250 ml of water was added, the organic layer was decanted and added in 30 minutes on 271.5 g of para benzyloxyaniline. The mixture was brought to reflux for 3 hours, filtered, washed with a 1 N hydrochloric acid solution, with water, dried, the solvent was evaporated and the residue was recrystallized in ethanol. 165.5 g of the product were obtained.

| Yield: | 81% | |
| --- | --- | --- |
| Melting point: | 107° C. | |
| NMR spectrum: | δ ppm (DMSO) | |
| | 9.80,s,—NH—COO— | 1 proton |
| | 7.40,s,and 5.08,s: | 7 protons |
| | 7.18,m,aromatic protons | 4 protons |
| | 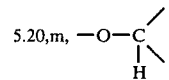 | 1 proton |
| | 3.85,d, (J = 5Hz) —CH$_2$—O— | 2 protons |
| | 3.59,m, Cl—CH$_2$—CH— | 3 protons |
| | 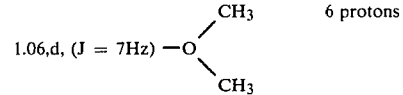 | 6 protons |
| IR spectrum: | band NH—COO at 1700 and 3305 cm$^{-1}$ | |

A solution of 165.5 g of this compound and 29.3 of potash in 2.4 liters of ethanol was brought to 50° C. for 3 hours. Then the solvent was evaporated, the residue was taken up in chloroform, washed with water, dried and the solvent was evaporated. The residue was crystallized in ether and recrystallized in dioxane. 113 g of product were obtained.

| Yield: | 75% |
| --- | --- |
| Melting point: | 110° C. |

| | | | |
|---|---|---|---|
| Empirical formula: | C$_{20}$H$_{23}$NO$_4$ | | |
| Molecular weight: | 341.4 | | |
| Elementary analysis: | | | |
| | C | H | N |
| Calculated (%) | 70.36 | 6.79 | 4.10 |
| Found (%) | 70.14 | 6.49 | 4.22 |

By the same method, but from the corresponding reagents, the compounds of formula (IX) were prepared, given in table (II) and bearing code numbers 226 to 229; as well as:

the compounds of formula (I) given in table I and bearing code numbers 187, 189 to 196, the compound of formula (Ib) given in table I and bearing code number 20, and the compound of formula (Va): mp=100° C.; Yield: 93%;

Empirical formula: C$_{24}$H$_{23}$NO$_4$; $[\alpha]_D^{21} = -33°$ 5 (C=1, CH$_2$Cl$_2$).

Second step: parahydroxyphenyl-3 isopropyloxymethyl-5 oxazolidinone-2 (VIII)

Code number: 221.

85 g of the compound prepared in the first step in 1700 ml of dioxane and 15 ml of 6.5 N hydrochloric alcohol, in the presence of 8.5 g of 10% palladium charcoal, were hydrogenolysed in an autoclave at a pressure of 6 kg for 6 hours. Then the mixture was filtered, the solvent was evaporated, the residue was crystallized in ether and recrystallized in toluene. 43.7 of product were obtained.

| | |
|---|---|
| Yield: | 70% |
| Melting point: | 93° C. |
| Empirical formula: | C$_{13}$H$_{17}$NO$_4$ |
| Molecular weight: | 251.3 |
| Elementary analysis: | |

| | C | H | N |
|---|---|---|---|
| Calculated (%) | 62.14 | 6.82 | 5.57 |
| Found (%) | 62.14 | 6.80 | 5.56 |

By the same method, but from the corresponding reagents, the compounds of formula (VIII) were prepared, given in table III and bearing code numbers: 222 to 224 and 230 to 232.

Third step: para n-butyloxyphenyl-3 isopropyloxy methyl-5 oxazolidinone-2 (I)

Code number: 47.

To a solution of 8.7 g of the compound obtained in the preceding step in 150 ml of dimethyl formamide, was added 1.68 g of sodium hydride (50%), then 9.7 g of n-butyl chloride. The mixture was brought to 100° C. for 2 hours and 30 mn, then the solvent was evaporated, the residue was taken up in chloroform, washed with water, dried, the solvent was evaporated, the residue was crystallized in isopropyl ether and recrystallized in isopropanol. 7.8 g of product were obtained.

| | |
|---|---|
| Yield: | 73% |
| Melting point: | 77° C. |
| Empirical formula: | C$_{17}$H$_{25}$NO$_4$ |
| Molecular weight: | 307.4 |
| Elementary analysis: | |

| | C | H | N |
|---|---|---|---|
| Calculated (%) | 66.42 | 8.20 | 4.56 |
| Found (%) | 66.19 | 8.27 | 4.36 |

By the same method, but from the corresponding reagents, the compounds of formula (I) were prepared, given in table I and bearing the following code numbers: 48, 50, 51, 58, 60, 62, 63, 142, 143, 152, 153, 157, 158, 160, 99 and 234, as well as the compound Formula (IIb): mp=132° C.; Yield: 97%; $[\alpha]_D^{20} = -79°$ 2 (C=1, pyridine: Empirical formula: C$_{18}$H$_{16}$N$_2$O$_4$;

| Elementary analysis: | | | |
|---|---|---|---|
| | C | H | N |
| Calculated (%) | 66.66 | 4.97 | 8.64 |
| Found (%) | 66.54 | 5.01 | 8.54 |

EXAMPLE 5 p-toluene sulfonyloxy-1 hydroxy-2 methoxy-3 propane (R configuration) (XII)

First step: methoxy-1 hydroxy-2 benzyloxy-3 propane R(+) (XIV)

To a solution of 4.14 g of benzyloxy-3 epoxy-1,2 propane in 40 ml of methanol, cooled to 5° C., were added 3 drops of boron trifluoride etherate. Then the mixture is left so as to reach slowly the room temperature (3 hours). A few gms. sodium bicarbonate was added, the solvent was evaporated, the residue was taken up in 200 ml of water, extracted with methylene chloride, dried on sodium sulfate and the solvent was evaporated. The residue was chromatographed by high performance liquid chromatography (HPLC) (SiO$_2$ 15–25$\mu$), the elution agent being a mixture of ethyl acetate (60%) and n-heptane (40%), and distillated BP$_{0.1}$=175° C. 70% of product were obtained. $[\alpha]_D^{20} = +44°$ 3 (C=5, ethanol). Empirical formula: C$_{11}$H$_{16}$O$_3$.

Second step: methoxy-3 propane diol-1,2 (S) (XIII)

A solution of 4.44 g of the compound obtained in the first step, in 200 ml of ethanol and 1 drop of hydrochloric ethanol, was hydrogenolised at a pressure of 5 kg and a temperature of 30° C., in the presence of 10% palladium charcoal. Then the mixture was filtered, a few gms. bicarbonate was added to the filtrate, the solvent was evaporated, the residue was taken up in ether, washed with water, dried on sodium sulfate, and the solvent was evaporated. 2.37 g of product were obtained after HPCL (SiO$_2$) of the crude product, the elution agent being a mixture of ethylacetate (60%) and n-heptane (40%).

Third step: toluene sulfonyloxy-1 hydroxy-2 methoxy-3 propane (R) (XII)

To a solution of 2.37 g of the compound obtained at the preceding step, in 10 ml of pyridine, cooled at 0° C., was slowly added a solution of 4.27 g of tosyl chloride in 50 ml of benzene. Then the mixture was left for 40 hours at room temperature, diluted with ether, filtered and the filtrate was washed with 1 N hydrochloric acid, then with water and with an aqueous solution of sodiim bicarbonate until neutrality. Then it was dried on sodium sulfate and the solvent was evaporated. The residue was chromatographed by HPLC (elution agent:

ethyl acetate: 60%; n-heptane 40%). Yield: 53%. The product obtained was directly used in the synthesis of the compound of formula (Ib) according to the method described in the first step of Example 4.

EXAMPLE 6 para benzyloxyphenyl-3 N-methylaminomethyl-5 oxazolidinone-2 (I)

Code number: 81

First step: mesylate of parabenzyloxyphenyl-3 hydroxymethyl-5 oxazolidinone-2 (XV)

To a solution of 28.5 g of para benzyloxyphenyl-3 hydroxymethyl-5 oxazolidinone-2 (IId) in 27 ml of triethylamine and 750 ml of methylene chloride cooled to 5° C., were added 15 ml of mesyl chloride. They were left for 15 minutes in contact, then the solution was concentrated, diluted with water and the precipitate was filtered and recrystallized in acetone. 32 g of product were obtained

| | |
|---|---|
| Yield: | 90% |
| Melting point: | 163° C. |
| Empirical formula: | $C_{18}H_{19}NO_6S$ |
| Molecular weight: | 377.41 |
| Elementary analysis: | |

| | C | H | N |
|---|---|---|---|
| Calculated (%) | 57.28 | 5.07 | 3.71 |
| Found (%) | 57.30 | 4.95 | 3.46 |

Second step: para benzyloxyphenyl-3 N-methylaminomethyl-5 oxazolidinone-2 [I]

A mixture of 29 g of the compound obtained at the preceding step and 50 g of ammonia in 500 ml of methanol, was heated to 110° C. for 6 hours in an autoclave. Then the solvent was evaporated, the residue was taken up in chloroform, washed with water, the solvent was evaporated and the residue was recrystallized in isopropanol. 17 g of product were isolated.

| | |
|---|---|
| Yield: | 74% |
| Melting point: | 124° C. |
| Empirical formula: | $C_{17}H_{18}N_2O_3$ |
| Molecular weight: | 298.33 |
| Elementary analysis: | |

| | C | H | N |
|---|---|---|---|
| Calculated (%) | 68.44 | 6.08 | 9.39 |
| Found (%) | 68.25 | 6.19 | 8.82 |

By the same method, but from the corresponding reagents, the compounds of formula (I) were prepared, given in table I and bearing the code numbers: 74 to 86; 170 to 176 and 201 to 207.

EXAMPLE 7

N-parabenzyloxyphenyl-1 hydroxymethyl-4 pyrrolidinone-2 (XVII)

First step: [(N-parabenzyloxyphenyl pyrrolidione-2) yl-4] carboxylic acid (XIX)

A mixture of 46 g of itaconic acid and 70 g of parabenzyloxyaniline in 400 ml of water was brought to reflux, then washed on the filter with chloroform, dried and recrystallized in acetone. 77 g of product were obtained.

| | |
|---|---|
| Yield: | 71% |
| Melting point: | 194° C. |
| Empirical formula: | $C_{18}H_{17}NO_4$ |
| Molecular weight: | 311.32 |
| Elementary analysis: | |

| | C | H | N |
|---|---|---|---|
| Calculated (%) | 69.44 | 5.50 | 4.50 |
| Found (%) | 69.69 | 5.48 | 4.80 |

Second step: [(N-parabenzyloxyphenyl pyrrolidinone-2) yl-4]ethyl carboxylate (XVIII)

A solution of 84 g of the acid obtained in the first step in 400 ml of ethanol and 6 ml of concentrated sulfuric acid was brought to reflux for 2 hours. Then, it was cooled, the precipitate was filtered, washed with water, dried and recrystallized in isopropanol. 47 g of product were obtained.

| | |
|---|---|
| Yield: | 51% |
| Melting point: | 106° C. |
| Empirical formula: | $C_{20}H_{21}NO_4$ |
| Molecular weight: | 339.38 |
| Elementary analysis: | |

| | C | H | N |
|---|---|---|---|
| Calculated (%) | 70.78 | 6.24 | 4.13 |
| Found (%) | 70.96 | 6.39 | 4.44 |

Third step: N-para benzyloxyphenyl-1 hydroxymethyl-4 pyrrolidinone-2 (XVII)

To a mixture of 7.9 g of sodium borohydride and 18 g of lithium bromide in 400 ml of diglyme, were added 70 g of the compound prepared at the preceeding step. Then the mixture was brught to 100° C. in 50 mn, diluted in 500 g of ice and 50 ml of concentrated hydrochloric acid, extracted with chloroform; the solvent was evaporated, the residue was crystallized in isopropyl ether and recrystallized in toluene. 45 g of product were obtained.

| | |
|---|---|
| Yield: | 72% |
| Melting point: | 110° C. |
| Empirical formula: | $C_{18}H_{19}NO_3$ |
| Molecular weight: | 297.34 |
| Elementary analysis: | |

| | C | H | N |
|---|---|---|---|
| Calculated (%) | 72.70 | 6.44 | 4.71 |
| Found (%) | 72.44 | 6.36 | 4.68 |

EXAMPLE 8

N-parabenzyloxyphenyl hydroxymethyl-3 pyrrolidine (I) Code number: 220

A solution of 53 g of the compound of formula (XVIII) obtained in example 7, in 300 ml of anhydrous tetrahydrofuran, was added while cooling to 11.8 g of lithium aluminum hydride (pellets) in 1000 ml of tetrahydrofuran. Then it was brought to reflux for 2 hours, then 6.3 ml of water, 4.75 ml of 20% NaOH and 22 ml of water were successively added. It was filtered, the filtrate was evaporated and the residue was crystallized in ethyl acetate. 38 g of product were obtained.

| Yield: | 85% |
| --- | --- |
| Melting point: | 87° C. |
| Empirical formula: | $C_{18}H_{21}NO_2$ |
| Elementary analysis: | |

|  | C | H | N |
| --- | --- | --- | --- |
| Calculated (%) | 76.29 | 7.47 | 4.94 |
| Found (%) | 76.40 | 7.60 | 4.65 |

EXAMPLE 9 para (metanitro) benzyloxyphenyl-3 methoxymethyl-5 thiazolidinone-2(I) Code number: 219

First step: para (metanitro) benzyloxyanilino-3 methoxy-1 propane thiol-2, oxalate (XX)

To a solution of 48.8 g of para (metanitro) benzyloxyaniline in 700 ml of isopropanol were slowly added 20.8 g of methoxymethyl-2 thiooxirane, and the mixture was brought to reflux for 7 hours. Then the solvent was evaporated, and the residue was chromatographed on a silica column. By eluting with methylene chloride, 38.4 g of an oil were obtained which were dissolved in acetonitrile. A solution of oxalic acid was added to acetonitrile, and the precipitate was filtered.

| Yield: | 43% |
| --- | --- |
| Melting point: | 120° C. |
| Empirical formula: | $C_{19}H_{22}N_2O_8S$ |
| Molecular weight: | 438.45 |
| Elementary analysis: | |

|  | C | H | N |
| --- | --- | --- | --- |
| Calculated (%) | 52.04 | 5.06 | 6.39 |
| Found (%) | 51.79 | 4.88 | 6.48 |

Second step: para (metanitro) benzyloxyphenyl-3 methoxymethyl-5 thiazolidinone-2 (I) Code number: 219

To a solution of 3 g of phosgene in 90 ml of dichloroethane, cooled to −10° C., was added 4.14 g of potassium carbonate then 6 g of the compound of formula (XX) (base form) obtained in the previous step, dissolved in 50 ml of dichlorethane, while maintaining the temperature between 5° and 10° C. Then, it came slowly to room temperature (3 hours), water was added, the organic phase was decanted, dried on sodium sulfate and the solvent was evaporated. The residue was crystallized in isopropyl ether, and recrystallized in isopropyl alcohol. 3 g of product were obtained.

| Yield: | 47% |
| --- | --- |
| Melting point: | 74° C. |
| Empirical formula: | $C_{18}H_{18}N_2O_5S$ |
| Elementary analysis: | |

|  | C | H | N |
| --- | --- | --- | --- |
| Calculated (%) | 57.74 | 4.85 | 7.48 |
| Found (%) | 57.45 | 4.97 | 7.18 |

EXAMPLE 10 para ethoxyphenyl-3 hydroxymethyl-5 oxazolidine thione-2 (I) Code number: 87

To a solution of 9.6 g of paraethoxyanilino-3 propanediol-1,2 (XXI) and 20.5 ml of triethylamine in 100 ml of tetrahydrofuran, were slowly added 5.2 g of thiophosgene while maintaining the temperature to 20° C. Then after 4 hours it was filtered, the filtrate was evaporated and the residue chromatographed on a silica column. Eluted with chloroform, 5.3 g of product were obtained.

| Yield: | 46% |
| --- | --- |
| Melting point: | 133° C. |
| Empirical formula: | $C_{12}H_{15}NO_3S$ |
| Molecular weight: | 253.31 |
| Elementary analysis: | |

|  | C | H | N |
| --- | --- | --- | --- |
| Calculated (%) | 56.89 | 5.97 | 5.53 |
| Found (%) | 56.98 | 6.14 | 5.54 |

By the same method, but from the corresponding reagents, the compounds of formula (I) were prepared, given in table I and bearing code numbers: 88 to 98; 100, 101, 102, 113 to 120; 177 and 208 to 218.

TABLE I $$\text{structure: } R\text{-}C_6H_4\text{-}N(CH_2\text{-}A(=X)\text{-}R_2)(R_1)$$ (I)

| Code Number | X | A | $R_1$ | $R_2$ | R | Empirical formula | Molecular weight | Melting point (°C.) | Yield (%) | Calculated C | Calculated H | Calculated N | Obtained C | Obtained H | Obtained N |
|---|---|---|---|---|---|---|---|---|---|---|---|---|---|---|---|
| 1 | Oxygen | Oxygen | H | $CH_2O$—$COCH_3$ | 4-$OCH_2$—CN | $C_{14}H_{14}N_2O_5$ | 290.27 | 92 | 72 | 57.93 | 4.86 | 9.65 | 57.90 | 4.87 | 9.42 |
| 2 | " | " | " | $CH_2OCOEt$ | " | $C_{15}H_{16}N_2O_5$ | 304.29 | 66 | 81 | 59.20 | 5.30 | 9.21 | 59.11 | 5.37 | 9.06 |
| 3 | " | " | " | $CH_2OCOCH_3$ | 4-O-CH₂-CN (cyclic) | " | 318.32 | 68 | 75 | 59.20 | 5.30 | 9.21 | 59.03 | 5.25 | 9.35 |
| 4 | " | " | " | $CH_2OCOEt$ | " | $C_{16}H_{18}N_2O_5$ | 318.32 | 66 | 80 | 60.37 | 5.70 | 8.80 | 60.44 | 5.54 | 8.64 |
| 5 | " | " | " | $CH_2OCO$-iPr | " | $C_{17}H_{20}N_2O_5$ | 332.34 | 72 | 58 | 61.43 | 6.07 | 8.43 | 61.14 | 6.23 | 8.37 |
| 6 | " | " | " | $CH_2OCOC_4H_{9n}$ | " | $C_{18}H_{22}N_2O_5$ | 346.37 | 65 | 72 | 62.41 | 6.40 | 8.09 | 62.70 | 6.59 | 7.94 |
| 7 | " | " | " | $CH_2OCO$-tBu | " | $C_{18}H_{22}N_2O_5$ | 346.37 | 90 | 57 | 62.41 | 6.40 | 8.09 | 62.29 | 6.21 | 7.90 |
| 8 | " | " | " | $CH_2OCO$-cyclohexyl | " | $C_{20}H_{24}N_2O_5$ | 372.41 | 104 | 76 | 64.50 | 6.50 | 7.52 | 64.35 | 6.30 | 7.69 |
| 9 | " | " | " | $CH_2OCOC_8H_{17n}$ | " | $C_{22}H_{30}N_2O_5$ | 402.48 | 75 | 75 | 65.65 | 7.51 | 6.96 | 65.41 | 7.35 | 6.72 |
| 10 | " | " | " | $CH_2OCO$-Ph | " | $C_{20}H_{18}N_2O_5$ | 366.36 | 150 | 68 | 65.56 | 4.95 | 7.65 | 65.27 | 4.82 | 7.55 |
| 11 | " | " | " | $CH_2OCOCH_3$ | 4 $OC_4H_{9,4}$ | $C_{16}H_{21}NO_5$ | 307.34 | 60 | 92 | 62.52 | 6.89 | 4.56 | 62.49 | 6.90 | 4.55 |
| 12 | " | " | " | $CH_2OCO$-tBu | " | $C_{19}H_{27}NO_5$ | 349.41 | 82 | 30 | 65.31 | 7.79 | 4.01 | 65.04 | 7.72 | 3.81 |
| 13 | " | " | " | $CH_2OCOCH_3$ | 4 O-CH₂-cyclopentyl | $C_{18}H_{23}NO_5$ | 333.37 | 94 | 85 | 64.85 | 6.95 | 4.20 | 64.91 | 7.24 | 4.05 |
| 14 | " | " | " | $CH_2OCOEt$ | " | $C_{19}H_{25}NO_5$ | 347.39 | 90 | 82 | 65.69 | 7.25 | 4.03 | 65.76 | 7.20 | 4.35 |

TABLE I-continued $$\underset{R}{\underset{|}{\overset{}{\bigcirc}}}\text{—N}\underset{X}{\overset{}{=}}\underset{A}{\overset{R_1\;R_2}{\diagup}}\quad (I)$$

| Code Number | X | A | R₁ R₂ | R | Empirical formula | Molecular weight | Melting point (°C.) | Yield (%) | \multicolumn{6}{c}{ELEMENTARY ANALYSIS} |
| | | | | | | | | | Calculated (%) | | | Obtained (%) | | |
| | | | | | | | | | C | H | N | C | H | N |
|---|---|---|---|---|---|---|---|---|---|---|---|---|---|---|
| 15 | " | " | " | CH₂OCO-⟨ | " | $C_{20}H_{27}NO_5$ | 361.42 | 78 | 54 | 66.46 | 7.53 | 3.88 | 66.21 | 7.51 | 3.66 |
| 16 | " | " | " | CH₂OCOC₄H₉n | " | $C_{21}H_{29}NO_5$ | 375.45 | 82 | 72 | 67.18 | 7.79 | 3.73 | 67.24 | 8.08 | 3.58 |
| 17 | " | " | " | CH₂OCO-⟨ | " | $C_{21}H_{29}NO_5$ | 375.45 | 94 | 66 | 67.18 | 7.79 | 3.73 | 67.19 | 7.92 | 3.54 |
| 18 | " | " | " | CH₂OCO-⟨ | " | $C_{23}H_{31}NO_5$ | 401.49 | 100 | 71 | 68.80 | 7.78 | 3.49 | 68.51 | 7.94 | 3.19 |
| 19 | " | " | " | CH₂OCOC₈H₁₇n | " | $C_{25}H_{37}NO_5$ | 431.55 | 78 | 62 | 69.57 | 8.64 | 3.25 | 69.76 | 8.91 | 3.10 |
| 20 | " | " | " | CH₂OCO-⟨ | " | $C_{23}H_{25}NO_5$ | 395.44 | 112 | 65 | 69.85 | 6.37 | 3.54 | 69.96 | 6.64 | 3.66 |
| 21 | " | " | " | CH₂OCOCH₃ | 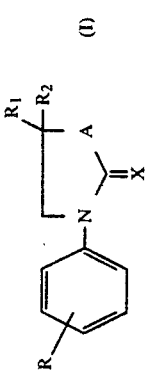 | $C_{19}H_{25}NO_5$ | 347.39 | 102 | 72 | 65.69 | 7.25 | 4.03 | 65.96 | 7.55 | 3.98 |
| 22 | " | " | " | CH₂OCOEt | " | $C_{20}H_{27}NO_5$ | 361.42 | 80 | 80 | 66.46 | 7.53 | 3.88 | 66.68 | 7.52 | 4.13 |
| 23 | " | " | " | CH₂OCOCH₃ | 4 O-⟨benzyl⟩ | $C_{19}H_{19}NO_5$ | 341.35 | 120 | 76 | 66.85 | 5.61 | 4.10 | 67.07 | 5.54 | 3.86 |
| 24 | " | " | " | CH₂OCOEt | " | $C_{20}H_{21}NO_5$ | 355.37 | 96 | 82 | 67.59 | 5.96 | 3.94 | 67.60 | 6.15 | 3.92 |
| 25 | " | " | " | CH₂OCO-⟨ | " | $C_{21}H_{23}NO_5$ | 369.40 | 114 | 65 | 68.28 | 6.28 | 3.79 | 68.31 | 6.40 | 3.73 |
| 26 | " | " | " | CH₂OCOC₄H₉n | " | $C_{22}H_{25}NO_5$ | 383.43 | 86 | 71 | 68.91 | 6.57 | 3.65 | 69.02 | 6.55 | 3.60 |
| 27 | " | " | " | CH₂OCO-⟨ | " | $C_{22}H_{25}NO_5$ | 383.43 | 116 | 52 | 68.91 | 6.57 | 3.65 | 69.16 | 6.63 | 3.55 |

TABLE I-continued $$\text{(I)}$$

| Code Number | X | A | R₁ | R₂ | R | Empirical formula | Molecular weight | Melting point (°C.) | Yield (%) | \multicolumn{6}{c}{ELEMENTARY ANALYSIS} |
|---|---|---|---|---|---|---|---|---|---|---|---|---|---|---|---|
| | | | | | | | | | | Calculated (%) | | | Obtained (%) | | |
| | | | | | | | | | | C | H | N | C | H | N |
| 28 | " | " | " | CH₂OCOC₈H₁₇n | " | C₂₆H₃₃NO₅ | 439.53 | 95 | 60 | 71.04 | 7.57 | 3.19 | 70.97 | 7.52 | 2.90 |
| 29 | " | " | " | CH₂OCO-⟨Ph⟩ | " | C₂₄H₂₁NO₅ | 403.42 | 128 | 69 | 71.45 | 5.25 | 3.47 | 71.26 | 5.08 | 3.15 |
| 30 | " | " | " | CH₂OCOCH₃ |  | C₁₉H₁₈ClNO₅ | 375.79 | 58 | 85 | 60.72 | 4.83 | 3.73 | 60.87 | 4.94 | 3.62 |
| 31 | " | " | " | CH₂OCOEt | " | C₂₀H₂₀ClNO₅ | 389.82 | 82 | 82 | 61.62 | 5.17 | 3.59 | 61.64 | 5.45 | 3.59 |
| 32 | " | " | " | CH₂OCO-iPr | " | C₂₁H₂₂ClNO₅ | 403.85 | 88 | 62 | 62.45 | 5.49 | 3.47 | 62.30 | 5.46 | 3.20 |
| 33 | " | " | " | CH₂OCOC₄H₉n | " | C₂₂H₂₄ClNO₅ | 417.88 | 95 | 73 | 63.23 | 5.79 | 3.35 | 63.27 | 5.69 | 3.17 |
| 34 | " | " | " | CH₂OCO-tBu | " | " | " | 92 | 65 | 63.23 | 5.79 | 3.35 | 63.22 | 5.67 | 3.25 |
| 35 | " | " | " | CH₂OCOC₈H₁₇n | " | C₂₆H₃₂ClNO₅ | 473.98 | 74 | 65 | 65.88 | 6.81 | 2.96 | 66.11 | 7.05 | 3.22 |
| 36 | " | " | " | CH₂OCOCH₃ |  | C₁₉H₁₈N₂O₇ | 386.35 | 126 | 72 | 59.06 | 4.70 | 7.25 | 59.10 | 4.56 | 6.95 |
| 37 | Oxygen | Oxygen | H | CH₂OCOEt | " | C₂₀H₂₀N₂O₇ | 400.38 | 106 | 75 | 59.99 | 5.03 | 7.00 | 59.86 | 5.03 | 6.71 |
| 38 | " | " | " | CH₂OCO-iPr | " | C₂₁N₂₂N₂O₇ | 414.40 | 108 | 58 | 60.86 | 5.35 | 6.76 | 60.62 | 5.45 | 6.49 |
| 39 | " | " | " | CH₂OCOC₄H₉n | " | C₂₂H₂₄N₂O₇ | 428.43 | 102 | 70 | 61.67 | 5.65 | 6.54 | 61.75 | 5.69 | 6.39 |

TABLE I-continued $$\text{(I)}$$

| Code Number | X | A | R₁ R₂ | | R | Empirical formula | Molecular weight | Melting point (°C.) | Yield (%) | ELEMENTARY ANALYSIS | | | | | |
|---|---|---|---|---|---|---|---|---|---|---|---|---|---|---|---|
| | | | | | | | | | | Calculated (%) | | | Obtained (%) | | |
| | | | | | | | | | | C | H | N | C | H | N |
| 40 | " | " | " | CH₂OCO-C(CH₃)₃ | " | C₂₂H₂₄N₂O₇ | 428.43 | 118 | 43 | 61.67 | 5.65 | 6.54 | 61.41 | 5.88 | 6.35 |
| 41 | " | " | " | CH₂OCO-C₆H₁₁ | " | C₂₄H₂₆N₂O₇ | 454.46 | 150 | 28 | 63.42 | 5.77 | 6.16 | 63.54 | 5.83 | 5.89 |
| 42 | " | " | " | CH₂OCOC₈H₁₇n | " | C₂₆H₃₂N₂O₇ | 484.53 | 83 | 65 | 64.45 | 6.66 | 5.78 | 64.18 | 6.82 | 5.64 |
| 43 | " | " | " | CH₂OCO-C₆H₅ | " | C₂₄H₂₀N₂O₇ | 448.42 | 182 | 60 | 64.28 | 4.50 | 6.25 | 64.39 | 4.39 | 6.17 |
| 44 | " | " | " | CH₂OCOEt | 4-O-CH₂-C₆H₄-F(3) | C₂₀H₂₀FNO₅ | 373.39 | 77 | 70 | 64.33 | 5.40 | 3.75 | 64.28 | 5.27 | 3.73 |
| 45 | " | " | " | CH₂OCH₃ | 3-CH₃ | C₁₂H₁₅NO₃ | 221.25 | 58 | 71 | 65.14 | 6.83 | 6.33 | 65.36 | 6.66 | 6.01 |
| 46 | " | " | " | " | 4 OC₄H₉n | C₁₅H₂₁NO₄ | 279.33 | 50 | 57 | 64.49 | 7.58 | 5.01 | 64.40 | 7.55 | 4.79 |
| 47 | " | " | " | CH₂O-CH(CH₃)₂ | " | C₁₇H₂₅NO₄ | 307.38 | 77 | 62 | 66.42 | 8.20 | 4.56 | 66.19 | 8.27 | 4.36 |
| 48 | " | " | " | CH₂O-C₆H₁₁ | " | C₂₀H₂₉NO₄ | 347.44 | 53 | 71 | 69.13 | 8.41 | 4.03 | 69.30 | 8.62 | 3.83 |
| 49 | " | " | " | CH₂OCH₃ | 4-O-CH₂-C₅H₉ | C₁₇H₂₃NO₄ | 305.36 | 70 | 48 | 66.86 | 7.59 | 4.59 | 66.79 | 7.47 | 4.44 |
| 50 | " | " | " | CH₂O-CH(CH₃)₂ | " | C₁₉H₂₇NO₄ | 333.41 | 66 | 35 | 68.44 | 8.16 | 4.20 | 68.54 | 8.39 | 4.22 |
| 51 | " | " | " | CH₂O-C₆H₁₁ | " | C₂₂H₃₁NO₄ | 373.47 | 67 | 59 | 70.75 | 8.37 | 3.75 | 70.63 | 8.53 | 3.85 |

TABLE I-continued

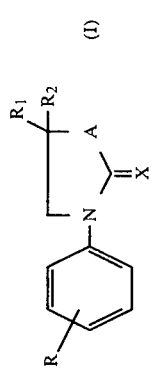

| Code Number | X | A | R₁ | R₂ | R | Empirical formula | Molecular weight | Melting point (°C.) | Yield (%) | ELEMENTARY ANALYSIS Calculated (%) C | H | N | Obtained (%) C | H | N |
|---|---|---|---|---|---|---|---|---|---|---|---|---|---|---|---|
| 52 | " | " | " | CH₂OCH₃ | 4-OCH₂CN | C₁₄H₁₆N₂O₄ | 276.28 | 104 | 57 | 60.86 | 5.84 | 10.14 | 60.59 | 5.50 | 10.11 |
| 53 | " | " | " | CH₂O-iPr | " | C₁₆H₂₀N₂O₄ | 304.34 | 89 | 39 | 63.14 | 6.62 | 9.21 | 63.29 | 6.73 | 9.36 |
| 54 | " | " | " | CH₂O-cyclohexyl | " | C₁₉H₂₄N₂O₄ | 344.39 | 80 | 42 | 66.26 | 7.02 | 8.13 | 66.19 | 6.88 | 7.98 |
| 55 | " | " | " | CH₂OCH₃ | 4-OCH₂-cyclohexyl | C₁₈H₂₅NO₄ | 319.39 | 90 | 63 | 67.69 | 7.89 | 4.39 | 67.96 | 7.83 | 4.39 |
| 56 | " | " | " | " | 4-OCH₂-cyclohexenyl | C₁₈H₂₃NO₄ | 317.37 | 80 | 55 | 68.12 | 7.30 | 4.41 | 68.21 | 7.61 | 4.39 |
| 57 | Oxygen | Oxygen | H | " | 4-OCH₂-phenyl | C₁₈H₁₉NO₄ | 313.34 | 90 | 83 | 68.99 | 6.11 | 4.47 | 69.19 | 6.07 | 4.24 |
| 58 | " | " | " | CH₂O-iPr | " | C₂₀H₂₃NO₄ | 341.39 | 110 | 75 | 70.36 | 6.79 | 4.10 | 70.14 | 6.49 | 4.22 |
| 59 | " | " | " | CH₂OCH₃ | 4-OCH₂-(3-Cl-phenyl) | C₁₈H₁₈ClNO₄ | 347.79 | 96 | 78 | 62.16 | 5.22 | 4.03 | 61.99 | 5.11 | 3.88 |
| 60 | " | " | " | CH₂O-iPr | " | C₂₀H₂₂ClNO₄ | 375.84 | 99 | 70 | 63.91 | 5.90 | 3.73 | 63.92 | 5.90 | 3.68 |

TABLE I-continued

Structure (I): Ar(R)-N(-A-C(=X))-CR₁R₂ type with formula (I)

| Code Number | X | A | R₁ | R₂ | R | Empirical formula | Molecular weight | Melting point (°C.) | Yield (%) | Calculated (%) C | H | N | Obtained (%) C | H | N |
|---|---|---|---|---|---|---|---|---|---|---|---|---|---|---|---|
| 61 | " | " | " | CH₂OCH₃ | 4-O-CH₂-C₆H₄-3-NO₂ | C₁₈H₁₈N₂O₆ | 358.34 | 78 | 62 | 60.33 | 5.06 | 7.82 | 60.52 | 5.10 | 7.92 |
| 62 | " | " | " | CH₂O-CH(CH₃)₂ | " | C₂₀H₂₂N₂O₆ | 386.39 | 74 | 60 | 62.16 | 5.74 | 7.25 | 62.16 | 5.94 | 7.49 |
| 63 | " | " | " | CH₂O-C₆H₁₁ (cyclohexyl) | " | C₂₃H₂₆N₂O₆ | 426.45 | 78 | 60 | 64.77 | 6.15 | 6.57 | 64.51 | 6.18 | 6.50 |
| 64 | " | " | " | CH₂OCH₃ | 4-O-CH₂-C₆H₄-F | C₁₈H₁₈FNO₄ | 331.33 | 106 | 55 | 65.25 | 5.48 | 4.23 | 65.37 | 5.52 | 4.20 |
| 65 | " | " | " | " | 4-O-CH₂-C₆H₄-3-CN | C₁₉H₁₈N₂O₄ | 338.35 | 88 | 65 | 67.44 | 5.36 | 8.28 | 67.41 | 5.48 | 8.37 |
| 66 | " | " | " | " | 4-O-CH₂-C₆H₄-3-CF₃ | C₁₉H₁₈F₃NO₄ | 381.34 | 83 | 60 | 59.84 | 4.76 | 3.67 | 59.81 | 4.62 | 3.70 |
| 67 | " | " | " | " | 4-O-CH₂-C₆H₄-3-F | C₁₈H₁₈FNO₄ | 331.33 | 79 | 60 | 65.25 | 5.48 | 4.23 | 65.20 | 5.59 | 4.13 |
| 68 | " | " | " | " | 4-O-CH₂-C₆H₄-Cl | C₁₈H₁₈ClNO₄ | 347.79 | 107 | 65 | 62.16 | 5.22 | 4.03 | 62.02 | 5.23 | 4.05 |

TABLE I-continued

| Code Number | X | A | $R_1$ $R_2$ | R | Empirical formula | Molecular weight | Melting point (°C.) | Yield (%) | ELEMENTARY ANALYSIS | | | | | |
|---|---|---|---|---|---|---|---|---|---|---|---|---|---|---|
| | | | | | | | | | Calculated (%) | | | Obtained (%) | | |
| | | | | | | | | | C | H | N | C | H | N |
| 69 | " | " | $CH_2OEt$ |  4 O | $C_{19}H_{20}N_2O_6$ | 372.37 | 50 | 48 | 61.28 | 5.41 | 7.52 | 61.10 | 5.34 | 7.48 |
| 70 | " | " | $CH_2OC_3H_{7n}$ | " | $C_{20}H_{22}N_2O_6$ | 386.39 | 52 | 75 | 62.16 | 5.74 | 7.25 | 62.09 | 5.63 | 7.06 |
| 71 | " | " | $CH_2O$― | " | $C_{20}H_{20}N_2O_6$ | 384.38 | <50 | 40 | 62.49 | 5.24 | 7.29 | 62.38 | 5.12 | 7.17 |
| 72 | " | " | $CH_2O$―≡ | " | $C_{20}H_{18}N_2O_6$ | 382.36 | 80 | 55 | 62.82 | 4.75 | 7.33 | 62.75 | 4.76 | 7.23 |
| 73 | " | " | $CH_2OCH_3$ | " | $C_{19}H_{20}N_2O_7$ | 388.37 | 79 | 50 | 58.76 | 5.19 | 7.21 | 58.53 | 5.26 | 7.20 |
| 74 | " | " | $CH_2$―$NHCH_3$ | $4\ OC_4H_{9n}$ | $C_{15}H_{22}N_2O_3$ | 278.34 | 56 | 75 | 64.72 | 7.97 | 10.07 | 64.57 | 7.81 | 10.18 |
| 75 | " | " | $CH_2$―N< | " | $C_{16}H_{24}N_2O_3$ | 292.37 | 68 | 70 | 65.73 | 8.27 | 9.58 | 65.73 | 8.01 | 9.49 |
| 76 | " | " | $CH_2$―$NH_2$ |  4 O | $C_{16}H_{22}N_2O_3$ | 290.35 | 97 | 72 | 66.18 | 7.64 | 9.65 | 66.33 | 7.96 | 9.79 |
| 77 | " | " | $CH_2$―$NHCH_3$ | " | $C_{17}H_{24}N_2O_3$ | 304.38 | 71 | 70 | 67.08 | 7.95 | 9.20 | 66.85 | 7.96 | 9.14 |
| 78 | " | " | $CH_2$―N< | " | $C_{18}H_{26}N_2O_3$ | 318.40 | 102 | 65 | 67.89 | 8.23 | 8.80 | 67.88 | 8.43 | 8.73 |
| 79 | " | " | $CH_2$―$NHCH_3$ |  4 O | $C_{16}H_{24}N_2O_3$ | 292.37 | 67 | 62 | 65.73 | 8.27 | 9.58 | 65.44 | 8.23 | 9.73 |
| 80 | " | " | $CH_2$―$NH_2$ |  4 O | $C_{17}H_{18}N_2O_3$ | 298.33 | 124 | 74 | 68.44 | 6.08 | 9.39 | 68.25 | 6.19 | 8.82 |

TABLE I-continued $$\text{R}\underset{}{\overset{}{\diagdown}}\text{—N}\overset{\text{R}_1\ \text{R}_2}{\underset{\text{X}}{\overset{|}{\text{—C—A}}}}\quad (I)$$

| Code Number | X | A | R₁ | R₂ | R | Empirical formula | Molecular weight | Melting point (°C.) | Yield (%) | ELEMENTARY ANALYSIS | | | | | |
|---|---|---|---|---|---|---|---|---|---|---|---|---|---|---|---|
| | | | | | | | | | | Calculated (%) | | | Obtained (%) | | |
| | | | | | | | | | | C | H | N | C | H | N |
| 81 | " | " | " | CH₂—NHCH₃ | | C₁₈H₂₀N₂O₃ | 312.36 | 88 | 71 | 69.21 | 6.45 | 8.97 | 69.51 | 6.36 | 8.42 |
| 82 | " | " | " | CH₂—NH₂ | 3-Cl benzyloxy | C₁₇H₁₇ClN₂O₃ | 332.78 | 122 | 70 | 61.35 | 5.15 | 8.42 | 61.04 | 5.20 | 7.66 |
| 83 | " | " | " | CH₂—NHCH₃ | | C₁₈H₁₉ClN₂O₃ | 346.81 | 72 | 55 | 62.33 | 5.52 | 8.08 | 61.93 | 5.35 | 8.35 |
| 84 | " | " | " | CH₂—NH₂ | 3-NO₂ benzyloxy | C₁₇H₁₇N₃O₅ | 343.33 | 88 | 50 | 59.47 | 4.99 | 12.24 | 59.21 | 4.71 | 12.54 |
| 85 | " | " | " | CH₂—NHCH₃ | | C₁₈H₁₉N₃O₅ | 357.36 | 70 | 75 | 60.49 | 5.36 | 11.76 | 60.18 | 5.39 | 11.83 |
| 86 | " | " | " | CH₂—N< | | C₁₉H₂₁N₃O₅ | 371.38 | 76 | 72 | 61.44 | 5.70 | 11.32 | 61.54 | 5.84 | 11.29 |
| 87 | Sulfur | " | " | —CH₂OH | 4-OEt | C₁₂H₁₅NO₃S | 253.31 | 133 | 46 | 56.89 | 5.97 | 5.53 | 56.98 | 6.14 | 5.54 |
| 88 | " | " | " | " | 4 OC₃H₇ₙ | C₁₃H₁₇NO₃S | 267.34 | 84 | 42 | 58.40 | 6.41 | 5.24 | 58.55 | 6.59 | 5.25 |
| 89 | " | " | " | " | 4 OC₄H₉ₙ | C₁₄H₁₉NO₃S | 281.37 | 95 | 55 | 59.76 | 6.81 | 4.98 | 59.64 | 6.80 | 4.86 |
| 90 | " | " | " | " | 4-O-cyclohexylmethyl | C₁₇H₂₃NO₃S | 321.43 | 100 | 40 | 63.52 | 7.21 | 4.36 | 63.27 | 7.01 | 4.15 |
| 91 | " | " | " | " | 4-O-isopentyl | C₁₅H₂₁NO₃S | 295.39 | 80 | 40 | 60.99 | 7.17 | 4.74 | 60.75 | 7.10 | 4.74 |
| 92 | " | " | " | " | 4-O-CH₂CH | C₁₂H₁₁N₂O₃S | 263.29 | 96 | 35 | 54.74 | 4.21 | 10.64 | 54.49 | 4.64 | 10.70 |

TABLE I-continued
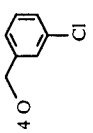
| Code Number | X | A | R₁ R₂ | R | Empirical formula | Molecular weight | Melting point (°C.) | Yield (%) | ELEMENTARY ANALYSIS | | | | | |
|---|---|---|---|---|---|---|---|---|---|---|---|---|---|---|
| | | | | | | | | | Calculated (%) | | | Obtained (%) | | |
| | | | | | | | | | C | H | N | C | H | N |
| 93 | " | " | " | 4-O-CH₂-C₆H₄-3-Cl | C₁₇H₁₆ClNO₃S | 349.83 | 132 | 40 | 58.36 | 4.61 | 4.00 | 58.17 | 4.61 | 4.00 |
| 94 | " | " | —CH₂—OH | 4-O-CH₂-C₆H₄-3-NO₂ | C₁₇H₁₆N₂O₅S | 360.38 | 142 | 37 | 56.65 | 4.48 | 7.77 | 56.36 | 4.29 | 7.58 |
| 95 | " | " | " | 4-O-CH₂-C₆H₄-4-Cl | C₁₇H₁₆ClNO₃S | 349.83 | 163 | 42 | 58.36 | 4.61 | 4.00 | 58.31 | 4.55 | 3.98 |
| 96 | " | " | " | 4-O-CH₂-C₆H₄-4-F | C₁₇H₁₆FNO₃S | 333.37 | 142 | 55 | 61.24 | 4.84 | 4.20 | 60.99 | 4.83 | 3.92 |
| 177 | " | " | " | 4-O-CH₂-C₆H₄-3-F | " | " | 153 | 37 | 61.24 | 4.84 | 4.20 | 60.94 | 4.78 | 4.10 |
| 97 | " | " | " | 4-O-CH₂-C₆H₄-3-CN | C₁₈H₁₆N₂O₃S | 340.39 | 162 | 40 | 63.51 | 4.74 | 8.23 | 63.30 | 5.00 | 8.08 |
| 98 | " | " | " | 4-O-CH₂-C₆H₄-3-CF₃ | C₁₈H₁₆F₃NO₃S | 383.38 | 95 | 52 | 56.39 | 4.21 | 3.65 | 56.08 | 4.14 | 3.30 |

TABLE I-continued structure (I): R-phenyl-N-CH2-C(=X)-A-C(R1)(R2)

| Code Number | X | A | R1 R2 | R | Empirical formula | Molecular weight | Melting point (°C.) | Yield (%) | Calculated (%) C | H | N | Obtained (%) C | H | N |
|---|---|---|---|---|---|---|---|---|---|---|---|---|---|---|
| 99 | Oxygen | —CH2— | H " | 4-O-CH2-(3-NO2-phenyl) | C18H18N2O5 | 342.34 | 96 | 85 | 63.15 | 5.30 | 8.18 | 62.98 | 5.31 | 7.96 |
| 100 | Sulfur | Oxygen | H " | 4-O-CH2-cyclopentyl | C16H21NO3S | 307.40 | 63 | 40 | 62.51 | 6.89 | 4.56 | 62.33 | 6.90 | 4.56 |
| 101 | " | " | " " | 4-O-CH2-cyclohexyl | C17H21NO3S | 319.41 | 112 | 35 | 63.92 | 6.63 | 4.39 | 63.64 | 6.76 | 4.17 |
| 102 | " | " | " " | 4-O-CH2CH2-CN | C13H14N2O3S | 278.32 | 108 | 43 | 56.10 | 5.07 | 10.07 | 55.80 | 5.05 | 9.87 |
| 103 | Oxygen | " | —CH2OCO-iPr | 4-O-CH2-cyclohexyl | C21H29NO5 | 375.45 | 98 | 76 | 67.18 | 7.79 | 3.73 | 67.45 | 7.87 | 3.97 |
| 104 | " | " | CH2OCOC4H9n | " | C22H31NO5 | 389.47 | 96 | 76 | 67.81 | 8.02 | 3.60 | 67.91 | 8.01 | 3.54 |
| 105 | " | " | CH2OCO-tBu | " | C22H31NO5 | 389.47 | 120 | 73 | 67.84 | 8.02 | 3.60 | 67.86 | 8.10 | 3.45 |
| 106 | " | " | CH2OCOEt | " | C20H20FNO5 | 373.37 | 77 | 80 | 64.33 | 5.40 | 3.75 | 64.28 | 5.27 | 3.73 |
| 107 | " | " | CH2OCO-iPr | 4-O-CH2-(3-F-phenyl) | C21H22FNO5 | 387.39 | 87 | 62 | 65.10 | 5.72 | 3.62 | 65.19 | 5.78 | 3.60 |
| 108 | " | " | CH2OCOC4H9n | " | C22H24FNO5 | 401.42 | 92 | 71 | 65.82 | 6.03 | 3.49 | 65.83 | 5.86 | 3.42 |
| 109 | " | " | CH2OEt | 4-OC4H9n | C16H23NO4 | 293.35 | 64 | 32 | 65.50 | 7.90 | 4.78 | 65.63 | 8.08 | 4.67 |
| 110 | " | " | CH2OCH3 | 4-O-CH2CH2-CN | C15H18N2O4 | 290.31 | 54 | 68 | 62.05 | 6.25 | 9.65 | 62.07 | 6.42 | 9.61 |

TABLE I-continued $$\underset{R}{\underset{\big|}{\text{C}_6\text{H}_4}}-N(CH_2\text{-Ph})-\underset{X}{\overset{A}{\overset{\|}{C}}}-\underset{R_2}{\overset{R_1}{C}}\qquad(I)$$

| Code Number | X | A | R₁ | R₂ | R | Empirical formula | Molecular weight | Melting point (°C.) | Yield (%) | Elementary Analysis Calculated (%) | | | Obtained (%) | | |
|---|---|---|---|---|---|---|---|---|---|---|---|---|---|---|---|
| | | | | | | | | | | C | H | N | C | H | N |
| 111 | " | " | H | CH₂OCH₃ | 4-O-CH₂CH(CH₃)₂ | C₁₆H₂₃NO₄ | 293.35 | 50 | 65 | 65.50 | 7.90 | 4.78 | 65.52 | 8.03 | 4.71 |
| 112 | O | O | " | " | 4-O-(CH₂)₄-CN | C₁₆H₂₀N₂O₄ | 304.34 | 78 | 50 | 63.14 | 6.62 | 9.21 | 63.00 | 6.45 | 9.09 |
| 113 | Sulfur | Oxygen | " | CH₂OH | 4-O-CH₂-(3-Cl,5-NO₂-Ph) | C₁₇H₁₅NClO₅S | 394.83 | 144 | 58 | 51.71 | 3.83 | 7.10 | 51.87 | 3.87 | 7.34 |
| 114 | " | " | " | CH₂OCH₃ | 4-O-cyclohexyl | C₁₈H₂₅NO₃S | 335.45 | 102 | 76 | 64.44 | 7.51 | 4.18 | 64.35 | 7.46 | 4.12 |
| 115 | " | " | " | CH₂OCOCH₃ | " | C₁₉H₂₅NO₄S | 363.46 | 96 | 52 | 62.78 | 6.93 | 3.85 | 62.64 | 7.00 | 3.85 |
| 116 | " | " | " | CH₂OCH₃ | 4-O-CH₂-(Ph-CN) | C₁₉H₁₈N₂O₃S | 354.42 | 108 | 61 | 64.38 | 5.12 | 7.90 | 64.37 | 4.82 | 7.76 |
| 117 | " | " | " | CH₂OCOCH₃ | 4-O-CH₂-(Ph-NO₂) | C₁₉H₁₈N₂O₆S | 402.42 | 104 | 71 | 56.71 | 4.51 | 6.96 | 56.91 | 4.28 | 6.73 |
| 118 | " | " | " | CH₂OCH₃ | " | C₁₈H₁₈N₂O₅S | 374.41 | 97 | 67 | 57.74 | 4.85 | 7.48 | 57.60 | 4.77 | 7.40 |
| 119 | " | " | " | CH₂OH | 4-O-tetrahydropyranyl-CH₂ | C₁₆H₂₁NO₄S | 323.40 | 117 | 58 | 59.42 | 6.55 | 4.33 | 59.17 | 6.62 | 4.26 |
| 120 | " | " | " | CH₂OCOCH₃ | 4-O-CH₂-(Ph-CN) | C₂₀H₁₈N₂O₄S | 382.43 | 99 | 82 | 62.81 | 4.74 | 7.33 | 62.88 | 4.67 | 7.33 |
| 121 | Oxygen | " | " | CH₂OCO-cyclohexyl | 4-O-CH₂-cyclohexyl | C₂₄H₃₃NO₅ | 415.51 | 128 | 87 | 69.37 | 8.01 | 3.37 | 69.33 | 7.99 | 3.29 |

TABLE I-continued

Structure (I):

$$\underset{R}{\underset{|}{C_6H_4}}-N(A)-C(=X)-C(R_1)(R_2)$$

| Code Number | X | A | R₁ | R₂ | R | Empirical formula | Molecular weight | Melting point (°C.) | Yield (%) | Elementary Analysis Calculated (%) C | H | N | Elementary Analysis Obtained (%) C | H | N |
|---|---|---|---|---|---|---|---|---|---|---|---|---|---|---|---|
| 122 | " | " | " | CH₂OCOC₈H₁₇n | 4-O-CH₂-cyclohexyl | C₂₆H₃₉NO₅ | 445.58 | 82 | 78 | 70.08 | 8.82 | 3.14 | 70.01 | 8.67 | 3.06 |
| 123 | " | " | " | CH₂OCOCH₃ | 4-O-isobutyl | C₁₇H₂₃NO₅ | 321.36 | 80 | 60 | 63.53 | 7.21 | 4.36 | 63.66 | 7.36 | 4.39 |
| 124 | " | " | " | CH₂OCOEt | " | C₁₈H₂₅NO₅ | 335.39 | 78 | 60 | 64.46 | 7.51 | 4.18 | 64.35 | 6.96 | 4.25 |
| 125 | " | " | " | CH₂OCO-t-Bu | " | C₂₀H₂₉NO₅ | 363.24 | 75 | 74 | 66.09 | 8.04 | 3.85 | 65.91 | 7.73 | 3.80 |
| 126 | " | " | " | CH₂OCOC₈H₁₇n | " | C₂₄H₃₇NO₅ | 419.54 | 67 | 72 | 68.70 | 8.89 | 3.34 | 68.41 | 8.93 | 3.19 |
| 127 | " | " | " | CH₂OCO-iPr | 4-O-isobutyl | C₁₉H₂₇NO₅ | 349.41 | 64 | 76 | 65.31 | 7.79 | 4.01 | 65.24 | 7.88 | 3.98 |
| 128 | " | " | " | CH₂OCOC₄H₉n | " | C₂₀H₂₉NO₅ | 363.44 | 70 | 64 | 66.09 | 8.04 | 3.85 | 65.96 | 7.85 | 3.70 |
| 129 | " | " | " | CH₂OCO-cyclohexyl | " | C₂₂H₃₁NO₅ | 389.48 | 81 | 68 | 67.84 | 8.02 | 3.60 | 67.66 | 8.03 | 3.71 |
| 130 | " | " | " | CH₂OCOCH₃ | 3-F-benzyl | C₁₉H₁₈FNO₅ | 359.34 | 60 | 65 | 63.50 | 5.04 | 3.89 | 63.28 | 5.14 | 3.70 |
| 131 | " | " | " | CH₂OCOC₈H₁₇n | " | C₂₆H₃₂FNO₅ | 457.52 | 73 | 73 | 68.24 | 7.05 | 3.06 | 68.30 | 6.96 | 3.16 |
| 132 | " | " | " | CH₂OCOEt | 3-CN-benzyl | C₂₁H₂₀N₂O₅ | 380.39 | 90 | 78 | 66.30 | 5.30 | 7.36 | 66.31 | 5.52 | 7.24 |
| 133 | " | " | " | CH₂OCOC₈H₁₇n | " | C₂₇H₃₂N₂O₅ | 464.54 | 72 | 77 | 69.80 | 6.94 | 6.03 | 69.63 | 7.15 | 5.91 |
| 134 | " | " | " | CH₂OCO-iPr | 3-NO₂-benzyl | C₂₂H₂₄N₂O₇ | 428.43 | 84 | 40 | 61.67 | 5.65 | 6.54 | 61.31 | 5.50 | 6.28 |

TABLE I-continued

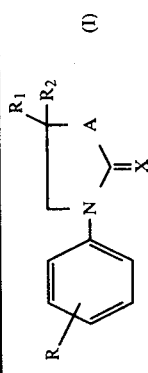

| Code Number | X | A | R₁ R₂ | R | Empirical formula | Molecular weight | Melting point (°C.) | Yield (%) | Calculated (%) C | H | N | Obtained (%) C | H | N |
|---|---|---|---|---|---|---|---|---|---|---|---|---|---|---|
| 135 | " | " | " CH$_2$OCOEt | 4-O-CH$_2$-C$_6$H$_4$-F | C$_{20}$H$_{20}$FNO$_5$ | 373.37 | 87 | 81 | 64.33 | 5.40 | 3.75 | 64.51 | 5.12 | 3.70 |
| 136 | " | " | " CH$_2$OCOC$_8$H$_{17n}$ | " | C$_{26}$H$_{32}$FNO$_5$ | 457.52 | 94 | 83 | 68.25 | 7.05 | 3.06 | 68.54 | 6.82 | 2.97 |
| 137 | " | " | " CH$_2$OCOEt | 4-O-CH$_2$-(3-Cl, 5-NO$_2$-C$_6$H$_3$) | C$_{20}$H$_{19}$ClN$_2$O$_7$ | 434.82 | 104 | 73 | 55.24 | 4.40 | 6.44 | 54.93 | 4.11 | 6.35 |
| 138 | " | " | " CH$_2$OCOC$_8$H$_{17n}$ | " | C$_{26}$H$_{31}$ClN$_2$O$_7$ | 518.99 | 102 | 87 | 60.17 | 6.02 | 5.40 | 60.02 | 5.82 | 5.35 |
| 139 | " | " | " CH$_2$OCOC$_8$H$_{17n}$ | 4-O-CH$_2$-(3-CN, 5-NO$_2$-C$_6$H$_3$) | C$_{27}$H$_{31}$N$_3$O$_7$ | 509.54 | 100 | 70 | 63.64 | 6.13 | 8.25 | 63.51 | 5.99 | 8.24 |
| 140 | " | " | " CH$_2$OCOEt | 4-O-CH$_2$-(C$_6$H$_4$-NO$_2$) | C$_{21}$H$_{19}$N$_3$O$_7$ | 425.39 | 145 | 50 | 59.29 | 4.50 | 9.88 | 58.67 | 4.33 | 9.78 |
| 141 | " | " | " CH$_2$OCOCH$_2$OCH$_3$ | " | C$_{20}$H$_{20}$N$_2$O$_8$ | 416.38 | 125 | 55 | 57.69 | 4.84 | 6.73 | 57.63 | 4.78 | 6.58 |
| 142 | " | " | " CH$_2$OC$_3$H$_{7n}$ | 4-O-C$_4$H$_{9n}$ | C$_{17}$H$_{25}$NO$_4$ | 307.38 | 72 | 52 | 66.42 | 8.20 | 4.56 | 66.35 | 8.39 | 4.72 |
| 143 | " | " | " " | 4-O-CH$_2$-cyclopentyl | C$_{19}$H$_{27}$NO$_4$ | 333.41 | 72 | 63 | 68.44 | 8.16 | 4.20 | 68.20 | 7.89 | 4.11 |
| 144 | " | " | " CH$_2$OCH$_3$ | 4-O-CH$_2$-(tetrahydropyranyl) | C$_{17}$H$_{23}$NO$_5$ | 321.36 | 100 | 81 | 63.53 | 7.21 | 4.36 | 63.36 | 7.09 | 4.27 |
| 145 | " | " | " CH$_2$OC$_3$H$_7$ | 4-O-CH$_2$-CH$_2$-CN | C$_{16}$H$_{20}$N$_2$O$_4$ | 304.34 | 40 | 38 | 63.14 | 6.62 | 9.21 | 62.96 | 6.31 | 8.96 |

TABLE I-continued

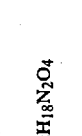
(I)

| Code Number | R | X | A | $R_1$ $R_2$ | Empirical formula | Molecular weight | Melting point (°C.) | Yield (%) | ELEMENTARY ANALYSIS Calculated (%) C H N | | | Obtained (%) C H N | | |
|---|---|---|---|---|---|---|---|---|---|---|---|---|---|---|
| 146 | 4-O-cyclopentyl-CH2 | " | " | " CH2OEt | $C_{18}H_{25}NO_4$ | 319.39 | 82 | 79 | 67.69 | 7.89 | 4.39 | 67.44 | 7.95 | 4.36 |
| 147 | 4-O-CH2CH2CN | " | " | " CH2OEt | $C_{15}H_{18}N_2O_4$ | 290.31 | 77 | 41 | 62.05 | 6.25 | 9.65 | 62.15 | 5.97 | 9.61 |
| 148 | 4-O-$C_5H_{11n}$ | " | " | " CH2OCH3 | $C_{16}H_{23}NO_4$ | 293.35 | 58 | 82 | 65.50 | 7.90 | 4.78 | 65.45 | 7.91 | 4.68 |
| 149 | 4-O-$C_6H_{13n}$ | " | " | " | $C_{17}H_{25}NO_4$ | 307.38 | ≦50 | 76 | 66.42 | 8.20 | 4.56 | 66.43 | 8.12 | 4.44 |
| 150 | 4-O-cycloheptyl | " | " | " | $C_{19}H_{27}NO_4$ | 333.41 | 71 | 32 | 68.44 | 8.16 | 4.20 | 68.35 | 8.17 | 4.37 |
| 151 | 4-O-CH2COCH3 | " | " | " | $C_{14}H_{17}NO_5$ | 279.28 | 58 | 85 | 60.20 | 6.14 | 5.02 | 59.94 | 6.02 | 5.11 |
| 152 | 4-O-CH2-C6H5 | " | " | " CH2OC3H7n | $C_{20}H_{23}NO_4$ | 341.39 | 105 | 67 | 70.36 | 6.79 | 4.10 | 70.17 | 6.80 | 3.86 |
| 153 | 4-O-CH2-C6H4-Cl | " | " | " | $C_{20}H_{22}ClNO_4$ | 375.84 | 75 | 71 | 63.91 | 5.90 | 3.73 | 63.95 | 6.07 | 3.93 |
| 154 | 4-O-CH2-C6H4-Cl | " | " | " CH2OEt | $C_{19}H_{21}NO_4$ | 327.37 | 105 | 85 | 69.70 | 6.47 | 4.28 | 69.44 | 6.48 | 4.23 |
| 155 | 4-O-CH2-C6H4-Cl | " | " | " | $C_{19}H_{20}ClNO_4$ | 361.81 | 81 | 82 | 63.07 | 5.57 | 3.87 | 62.89 | 5.38 | 3.80 |
| 156 | 4-O-CH2-C6H3(Cl)(NO2) | " | " | " CH2OCH3 | $C_{18}H_{17}ClN_2O_6$ | 392.79 | 110 | 64 | 55.04 | 4.36 | 7.13 | 54.98 | 4.35 | 7.17 |

TABLE I-continued (I) structure with N-phenyl (R substituent) linked to C(=X)-A-C(R₁)(R₂)

| Code Number | X | A | R₁ R₂ | R | Empirical formula | Molecular weight | Melting point (°C.) | Yield (%) | Calculated (%) C | H | N | Obtained (%) C | H | N |
|---|---|---|---|---|---|---|---|---|---|---|---|---|---|---|
| 157 | " | " | CH₂O—CH₂CH(CH₃)₂ | 4-O-CH₂-C₆H₄-3-NO₂ | C₂₁H₂₄N₂O₆ | 400.42 | 76 | 62 | 62.99 | 6.04 | 7.00 | 62.68 | 5.79 | 6.85 |
| 158 | " | " | CH₂O—CH₂CH₂CH(CH₃)₂ | " | C₂₂H₂₆N₂O₆ | 414.44 | 70 | 59 | 63.75 | 6.32 | 6.76 | 63.49 | 6.11 | 6.62 |
| 159 | " | " | CH₂OCH₃ | 4-O-CH₂-C₆H₄-4-CN | C₁₉H₁₈N₂O₄ | 338.35 | 110 | 78 | 67.44 | 5.36 | 8.28 | 67.21 | 5.06 | 8.20 |
| 160 | " | " | CH₂OC₃H₇n | 4-O-CH₂-C₆H₄-4-CN | C₂₁H₂₂N₂O₄ | 366.40 | 75 | 60 | 68.83 | 6.05 | 7.65 | 68.51 | 5.98 | 7.67 |
| 161 | " | " | CH₂OCH₃ | 4-O-CH₂-C₆H₃-2-CN-5-NO₂ | C₁₉H₁₇N₃O₆ | 383.35 | 163 | 52 | 59.63 | 4.47 | 10.96 | 59.50 | 4.60 | 10.85 |
| 162 | " | " | " | 4-O-CH₂-C₆H₃-2-CN-F | C₁₉H₁₇FN₂O₄ | 356.34 | 93 | 58 | 64.04 | 4.81 | 7.86 | 63.78 | 4.80 | 7.71 |
| 163 | " | " | " | 4-O-CH₂-C₆H₃-CN-Cl | C₁₈H₁₇ClFNO₄ | 365.78 | 90 | 34 | 59.10 | 4.68 | 3.83 | 59.40 | 4.55 | 4.07 |
| 164 | " | " | " | 4-O-CH₂-C₆H₃-Cl-Cl | C₁₈H₁₇Cl₂NO₄ | 382.24 | 93 | 83 | 56.56 | 4.48 | 3.66 | 56.45 | 4.23 | 3.66 |
| 165 | " | " | " | 4-O-CH₂-C₆H₄-4-NO₂ | C₁₈H₁₈N₂O₆ | 358.34 | 134 | 75 | 60.33 | 5.06 | 7.82 | 60.08 | 4.74 | 7.55 |

TABLE I-continued $$\text{R} \underset{\text{N}}{\overset{}{\bigcirc\!\!\!-\!\!\!\bigcirc}} \underset{\text{R}_2}{\overset{\text{R}_1}{-\text{C}}} \overset{\text{A}}{\underset{\text{X}}{=}} \quad (I)$$

| Code Number | R | X | A | R₁ R₂ | Empirical formula | Molecular weight | Melting point (°C.) | Yield (%) | ELEMENTARY ANALYSIS | | | | | |
|---|---|---|---|---|---|---|---|---|---|---|---|---|---|---|
| | | | | | | | | | Calculated (%) | | | Obtained (%) | | |
| | | | | | | | | | C | H | N | C | H | N |
| 166 | 4-O-CH₂-(3,5-Cl₂-phenyl) | " | " | " " | $C_{18}H_{17}Cl_2NO_4$ | 382.24 | 76 | 69 | 56.56 | 4.48 | 3.66 | 56.47 | 4.46 | 3.73 |
| 167 | 4-O-CH₂-(phenyl-CN) | " | " | " CH₂OEt | $C_{20}H_{20}N_2O_4$ | 352.38 | ≦50 | 57 | 68.17 | 5.72 | 7.95 | 67.93 | 5.50 | 8.04 |
| 168 | 4-O-CH₂-(Cl,CH₃-phenyl) | " | " | " CH₂OCH₃ | $C_{18}H_{17}ClN_2O_6$ | 392.79 | 94 | 67 | 55.04 | 4.36 | 7.13 | 55.04 | 4.25 | 7.40 |
| 169 | 4-O-CH₂-(NO₂,F-phenyl) | " | " | " " | $C_{18}H_{17}FN_2O_6$ | 376.33 | 95 | 61 | 57.44 | 4.55 | 7.44 | 57.30 | 4.56 | 7.29 |
| 170 | 4-OC₄H₉ₙ | " | " | " CH₂NH₂ | $C_{14}H_{20}N_2O_3$ | 264.32 | 90 | 26 | 63.61 | 7.63 | 10.60 | 63.31 | 7.47 | 10.60 |
| 171 | 4-O-CH₂-CH₂-CN | " | " | " CH₂N(CH₃)₂ | $C_{15}H_{19}N_3O_3$ | 289.33 | 97 | 17 | 62.26 | 6.62 | 14.52 | 62.43 | 6.52 | 14.46 |
| 172 | 4-O-CH₂-cyclohexyl | " | " | " CH₂NH₂ | $C_{17}H_{24}N_2O_3$ | 304.38 | 98 | 43 | 67.08 | 7.95 | 9.20 | 67.15 | 7.87 | 8.92 |
| 173 | " | " | " | " CH₂NHCH₃ | $C_{18}H_{26}N_2O_3$ | 318.40 | 96 | 32 | 67.89 | 8.23 | 8.30 | 68.29 | 8.17 | 3.30 |
| 174 | 4-O-CH₂-CH₂-CH(CH₃)₂ | " | " | " CH₂NH₂ | $C_{15}H_{22}N_2O_3$ | 278.34 | 84 | 45 | 64.72 | 7.97 | 10.07 | 64.80 | 7.91 | 10.16 |
| 175 | 4-O-CH₂-(F-phenyl) | " | " | " CH₂NHCH₃ | $C_{18}H_{19}N_2O_3F$ | 330.35 | 85 | 36 | 65.44 | 5.80 | 8.40 | 65.45 | 5.82 | 8.34 |

TABLE I-continued structure (I): R-phenyl-N(CH2-)-A(R1)(R2)-C(=X)- ... general formula (I)

| Code Number | R | X | A | R1 | R2 | Empirical formula | Molecular weight | Melting point (°C.) | Yield (%) | Calculated (%) C | Calculated (%) H | Calculated (%) N | Obtained (%) C | Obtained (%) H | Obtained (%) N |
|---|---|---|---|---|---|---|---|---|---|---|---|---|---|---|---|
| 176 | " | " | " | " | CH₂NH₂ | C₁₇H₁₇N₂O₂F | 316.32 | 129 | 29 | 44.54 | 5.42 | 8.86 | 64.29 | 5.46 | 8.65 |
| 178 | " | O | O | " | CH₂OCO—CH₂O—C₆H₅ (with NO₂) | C₂₅H₂₂N₂O₈ | 478.44 | 120 | 64 | 62.76 | 4.64 | 5.86 | 62.89 | 4.66 | 5.84 |
| 179 | 4 O—CH₂—CH=CH—CH₃ | " | " | " | CH₂OCH₃ | C₁₅H₁₉NO₄ | 277.31 | 63 | 74 | 64.96 | 6.91 | 5.05 | 64.67 | 6.77 | 4.97 |
| 180 | 4 O—CH₂—CH=CH—N(CH₃)₂ | " | " | " | " | C₁₃H₁₈N₂O₃ | 250.29 | 92 | 59 | 62.38 | 7.25 | 11.19 | 62.45 | 6.98 | 10.94 |
| 181 | 4 O—CH₂CH₂-morpholinyl | " | " | " | " | C₁₇H₂₄N₂O₅ | 336.38 | 92 | 75 | 60.70 | 7.19 | 8.33 | 60.47 | 7.04 | 8.10 |
| 182 | 4 O—CH₂-tetrahydropyranyl | " | " | " | " | C₁₇H₂₃NO₅ | 321.36 | 77 | 22 | 63.53 | 7.21 | 4.36 | 63.67 | 7.23 | 4.38 |
| 183 | 4 O—CH₂-cyclobutyl | " | " | " | " | C₁₆H₂₁NO₄ | 291.34 | 81 | 31 | 65.96 | 7.27 | 4.81 | 66.00 | 7.46 | 4.71 |
| 184 | 4 O—CH₂-cyclopentenyl | " | " | " | " | C₁₇H₂₁NO₄ | 303.35 | 83 | 33 | 67.31 | 6.98 | 4.62 | 67.01 | 7.08 | 4.43 |
| 185 | 4 O—CH₂—CH=C(CH₃)₂ | " | " | " | " | C₁₆H₂₁NO₄ | 291.34 | 84 | 78 | 65.96 | 7.27 | 4.81 | 66.03 | 7.28 | 4.29 |
| 234 | 4 O—(CH₂)₄Cl | " | " | " | " | C₁₅H₂₀ClNO₄ | 313.77 | 58 | 66 | 57.41 | 6.42 | 4.46 | 57.05 | 6.50 | 4.50 |

TABLE I-continued $$\underset{R}{\text{Ar}}\overset{R_1}{\underset{N}{\bigvee}}\overset{R_2}{\underset{X}{\bigvee}}\quad (I)$$

| Code Number | X | A | R₁ | R₂ | R | Empirical formula | Molecular weight | Melting point (°C.) | Yield (%) | ELEMENTARY ANALYSIS Calculated (%) C H N | Obtained (%) C H N |
|---|---|---|---|---|---|---|---|---|---|---|---|
| 186 | " | " | " | " |  4-O-CH₂-cyclopentyl | C₁₈H₂₅NO₄ | 319.39 | 77 | 22 | 67.69 7.89 9.39 | 67.62 8.03 4.25 |
| 187 | " | " | " | " |  trans, 4- | C₁₉H₁₉NO₃ | 309.35 | 166 | 26 | 73.76 6.19 4.53 | 73.52 6.10 4.38 |
| 188 | " | " | " | CH₂OCH₃ | 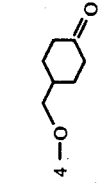 4-O-CH₂-cyclohexanone | C₁₈H₂₃NO₅ | 333.37 | 102 | 70 | 64.85 6.95 4.20 | 64.82 7.11 4.19 |
| 189 | " | " | " | " |  4-C≡C-phenyl | C₁₉H₁₇NO₃ | 307.33 | 120 | 50 | 74.25 5.58 4.56 | 74.18 5.30 4.47 |
| 190 | " | " | " | " |  trans, Cl, 4- | C₁₉H₁₈NO₃Cl | 343.80 | 136 | 30 | 66.37 5.28 4.07 | 66.08 5.24 3.90 |
| 191 | " | " | " | " |  trans, NO₂, 4- | C₁₉N₁₈N₂O₅ | 354.35 | 110 | 50 | 64.40 5.12 7.91 | 64.17 5.24 7.96 |
| 192 | " | " | " | " | 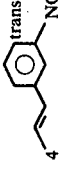 4-CH₂CH₂-phenyl | C₁₉H₂₁NO₃ | 311.37 | 74 | 62 | 73.29 6.80 4.50 | 73.17 6.93 4.53 |
| 193 | " | " | " | " | 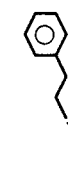 cis, 4- | C₁₉H₁₉NO₃ | 309.35 | 82 | 60 | 73.16 6.19 4.63 | 73.47 6.10 4.50 |
| 194 | " | " | " | " | 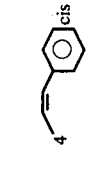 cis, NO₂, 4- | C₁₉H₁₈N₂O₅ | 354.35 | Oil | 40 | 64.40 5.12 7.91 | 64.25 5.27 7.92 |

TABLE I-continued (I) structure: R-phenyl-N(CH2-C(R1)(R2)-A-C(=X)-)

| Code Number | X | A | R1 R2 | R | Empirical formula | Molecular weight | Melting point (°C.) | Yield (%) | Calculated (%) C | H | N | Obtained (%) C | H | N |
|---|---|---|---|---|---|---|---|---|---|---|---|---|---|---|
| 195 | " | " | " | 4-cyclohexyl-phenyl | C17H17NO3 | 283.31 | 120 | 75 | 72.06 | 6.05 | 4.94 | 72.27 | 5.91 | 4.62 |
| 196 | " | " | " | 2-CN, 4-trans-CH=CH-phenyl | C20H18N2O3 | 334.36 | 127 | 70 | 71.84 | 5.43 | 8.38 | 71.89 | 5.36 | 8.45 |
| 197 | " | " | " | 2-Br, 4-OCH2-phenyl | C18H18BrNO4 | 392.24 | 116 | 81 | 55.11 | 4.63 | 3.57 | 54.94 | 4.35 | 3.55 |
| 198 | " | " | " | 2-I, 4-OCH2-phenyl | C18H18NIO4 | 439.24 | 118 | 78 | 49.22 | 4.13 | 3.19 | 49.39 | 4.08 | 3.13 |
| 199 | " | " | " | 2-CN, 4-OCH2-phenyl R(−) | C19H18N2O4 [α]D20 = −39°7 | 338.35 (C = 1/CH2Cl2) | 83 | 75 | 67.44 | 5.36 | 8.28 | 67.14 | 5.53 | 8.38 |
| 200 | " | " | " | 2-CN, 4-OCH2-cyclohexyl S(+) | C19H18N2O4 [α]D20 = +32°1 | 338.35 (C = 1/CH2Cl2) | 84 | 51 | 67.44 | 5.36 | 8.28 | 67.52 | 5.36 | 8.28 |
| 201 | " | " | CH2—NH—iPr | 2-NO2, 4-OCH2-phenyl | C20H23N3O5 | 385.41 | 76 | 36 | 62.32 | 6.02 | 10.90 | 62.04 | 5.90 | 10.75 |
| 202 | " | " | CH2—N(morpholino) | " | C21H23N3O6 | 413.42 | 138 | 26 | 61.01 | 5.61 | 10.17 | 61.11 | 5.67 | 10.01 |
| 203 | " | " | CH2—NH—Et | " | C19H21N3O5 | 371.38 | 70 | 54 | 61.44 | 5.70 | 11.32 | 61.48 | 5.58 | 11.57 |

TABLE I-continued $$\underset{R}{\underset{|}{\bigcirc}}-N(CH_2)-\underset{R_2}{\overset{R_1}{C}}-A-\underset{X}{\overset{\|}{C}} \quad (I)$$

| Code Number | X | A | R₁ R₂ | R | Empirical formula | Molecular weight | Melting point (°C.) | Yield (%) | Calculated (%) C | H | N | Obtained (%) C | H | N |
|---|---|---|---|---|---|---|---|---|---|---|---|---|---|---|
| 204 | " | " | CH₂—N(piperidine) | " | C₂₁H₂₃N₃O₅ | 397.42 | 110 | 24 | 63.46 | 5.83 | 10.57 | 63.16 | 5.90 | 10.39 |
| 205 | " | " | CH₂—NH₂ | 4 O—CH₂—C₆H₄—CN | C₁₈H₁₇N₃O₃ | 323.34 | 94 | 10 | 66.86 | 5.30 | 13.00 | 66.73 | 5.58 | 12.69 |
| 206 | " | " | CH₂—N(CH₃)₂ | " | C₂₀H₂₁N₃O₃ | 351.39 | 84 | 62 | 68.36 | 6.02 | 11.96 | 68.38 | 6.30 | 11.68 |
| 207 | " | " | CH₂—NH₂ | 4 O—CH₂—C₆H₃(Cl)(NO₂) | C₁₇H₁₆ClN₃O₅ | 475.06 | 155 | 11 | 54.04 | 4.27 | 11.12 | 54.17 | 4.31 | 11.26 |
| 208 | S | " | CH₂OCO Et | 4 O—CH₂—C₆H₄—NO₂ | C₂₀H₂₀N₂O₆S | 416.44 | 126 | 73 | 57.68 | 4.84 | 6.73 | 57.59 | 5.03 | 6.69 |
| 209 | " | " | CH₂OH | 4 O—CH₂—C₆H₃(CN)(F) | C₁₈H₁₅FN₂O₃S | 358.38 | 126 | 27 | 59.57 | 4.31 | 7.72 | 59.72 | 4.52 | 7.54 |
| 210 | " | " | CH₂OC₃H₇ₙ | 4 O—CH₂—C₆H₄—NO₂ | C₂₀H₂₂N₂O₅S | 402.46 | 110 | 57 | 59.68 | 5.51 | 6.96 | 59.57 | 5.65 | 7.19 |
| 211 | " | " | CH₂OCH₃ | 4 O—CH₂-cyclopentyl | C₁₇H₂₃NO₃S | 321.43 | 68 | 35 | 63.52 | 7.21 | 4.36 | 63.61 | 7.43 | 4.33 |
| 212 | " | " | CH₂OH | 4 O—(CH₂)₃—CN | C₁₄H₁₆N₂O₃S | 292.35 | 80 | 54 | 57.51 | 5.52 | 9.58 | 57.40 | 5.32 | 9.42 |

TABLE I-continued $$\text{structure (I)}$$

| Code Number | X | A | R₁ R₂ | R | Empirical formula | Molecular weight | Melting point (°C.) | Yield (%) | Calculated C | Calculated H | Calculated N | Obtained C | Obtained H | Obtained N |
|---|---|---|---|---|---|---|---|---|---|---|---|---|---|---|
| 213 | " | " | " CH₂OCH₃ | 4 O—CH₂-(3-pyridyl) | C₁₇H₁₈N₂O₃S | 460.95 | 133 | 17 | 51.85 | 4.57 | 6.08 | 51.68 | 4.40 | 6.04 |
| 214 | " | " | " " | 4 O—CH₂CH₂CH(CH₃)₂ | C₁₆H₃₃NO₃S | 309.42 | Oil | 30 | 62.10 | 7.49 | 4.53 | 62.41 | 7.61 | 4.45 |
| 215 | " | " | " CH₂OH | 4 O—(CH₂)₄—CN | C₁₅H₁₈N₂O₃S | 306.37 | 106 | 40 | 58.80 | 5.92 | 9.14 | 58.88 | 5.74 | 9.12 |
| 216 | " | " | " CH₂O Et | 4 O—CH₂-(4-NO₂-phenyl) | C₁₉H₂₀N₂O₅S | 388.43 | 80 | 47 | 58.75 | 5.19 | 7.21 | 58.68 | 5.09 | 7.28 |
| 217 | " | " | " CH₂O CH₃ | 4 O—(CH₂)₄—CN | C₁₆H₂₀N₂O₃S | 320.40 | Oil | 24 | 59.97 | 6.29 | 8.74 | 59.81 | 6.28 | 9.02 |
| 218 | " | " | " " | 4 O—CH₂-(3-NO₂-5-CN-phenyl) | C₁₉H₁₇N₃O₅S | 399.42 | 176 | 57 | 57.13 | 4.29 | 10.52 | 57.06 | 4.19 | 10.46 |
| 219 | O | S | " " | 4 O—CH₂-(3-NO₂-phenyl) | C₁₈H₁₈N₂O₅S | 374.41 | 74 | 47 | 57.74 | 4.85 | 7.48 | 57.45 | 4.97 | 7.18 |
| 220 | H₂ | CH₂ | " CH₂OH | 4 O—CH₂-phenyl | C₁₈H₂₁NO₂ | 283.36 | 87 | 85 | 76.29 | 7.47 | 4.94 | 76.40 | 7.60 | 4.65 |

TABLE II

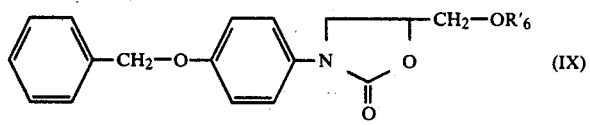

| Code Number | R6 | Empirical Formula | Molecular Weight | Melting Point (°C.) | Yield % | Elementary Analysis | % C | H | N |
|---|---|---|---|---|---|---|---|---|---|
| 226 | —C3H7n | C20H23NO4 | 341.39 | 105 | 62 | Cal. | 70.36 | 6.79 | 4.10 |
|  |  |  |  |  |  | Obt. | 70.17 | 6.80 | 3.86 |
| 227 | —Et | C19H21NO4 | 327.37 | 105 | 58 | Cal. | 69.70 | 6.47 | 4.28 |
|  |  |  |  |  |  | Obt. | 69.44 | 6.48 | 4.23 |
| 228 | —CH2—⟨ | C21H25NO4 | 355.42 | 107 | 61 | Cal. | 70.96 | 7.09 | 3.94 |
|  |  |  |  |  |  | Obt. | 71.09 | 6.77 | 3.70 |
| 229 | —CH2—CH2—⟨ | C22H27NO4 | 369.44 | 101 | 61 | Cal. | 71.52 | 7.37 | 3.79 |
|  |  |  |  |  |  | Obt. | 71.71 | 7.41 | 3.83 |

TABLE III

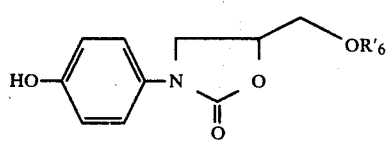

(VIII)

| Code Number | R'6 | Empirical Formula | Molecular Weight | Melting Point (°C.) | Yield (%) | ELEMENTARY ANALYSIS | C | H | N |
|---|---|---|---|---|---|---|---|---|---|
| 221 | —⟨ | C13H17NO4 | 251.27 | 93 | 70 | Cal. | 62.14 | 6.82 | 5.57 |
|  |  |  |  |  |  | Obt. | 62.14 | 6.80 | 5.56 |
| 222 | CH3 | C11H13NO4 | 223.22 | 106 | 81 | Cal. | 59.18 | 5.87 | 6.28 |
|  |  |  |  |  |  | Obt. | 59.15 | 6.01 | 6.38 |
| 223 | cyclohexyl | C16H21NO4 | 291.34 | 108 | 92 | Cal. | 65.96 | 7.27 | 4.81 |
|  |  |  |  |  |  | Obt. | 66.17 | 7.58 | 5.01 |
| 224 | —C3H7n | C13H17NO4 | 251.27 | 88 | 78 | Cal. | 62.14 | 6.82 | 5.57 |
|  |  |  |  |  |  | Obt. | 62.16 | 6.53 | 5.80 |

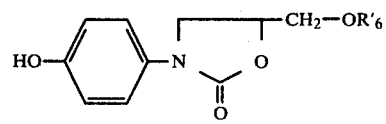

| Code Number | R'6 | Empirical Formula | Molecular Weight | Melting Point (°C.) | Yield % | ELEMENTARY ANALYSIS | % C | H | N |
|---|---|---|---|---|---|---|---|---|---|
| 230 | —Et | C12H15NO4 | 237.25 | 86 | 81 | Cal. | 60.75 | 6.37 | 5.90 |
|  |  |  |  |  |  | Obt. | 60.60 | 6.21 | 5.83 |
| 231 | —CH2—⟨ | C14H19NO4 | 265.30 | 98 | 85 | Cal. | 63.38 | 7.22 | 5.28 |
|  |  |  |  |  |  | Obt. | 63.28 | 7.04 | 5.39 |
| 232 | —CH2—CH2—⟨ | C15H21NO4 | 279.33 | 80 | 82 | Cal. | 64.49 | 7.58 | 5.01 |
|  |  |  |  |  |  | Obt. | 64.30 | 7.42 | 4.84 |

The compounds of formula (I) were studied on laboratory animals and showed activities in the psychotropic field, as potential anti-depressants.

These activities were revealed in the following tests:
Test A: Potentiation in mice of generalized trembling caused by an interperitoneal injection (200 mg/kg) of dl-5-hydroxytryptophane, following the protocol described by C. Gouret and G. Raynaud in J. Pharmacol. (Paris), (1974), 5, 231.

Test B: Antagonism with respect to the ptosis observed one hour after an intravenous injection (2 mg/kg) of reserpine given to mice, following the protocol described by C. Gouret and J. Thomas in J. Pharmacol. (Paris), 1973, 4, 401.

The results of these two tests, as well as those of a well-know reference substance, Toloxatone, are collected in Table IV below:

TABLE VI / TABLE VI-continued

| Compound tested Code Number | Test A ED/50/ mg/kg/po | Test B ED/50/ mg/kg/po | Toxicity LD/50 Mouse /mg/kg/po |
|---|---|---|---|
| 1 | 12.5 | 6.2 | |
| 2 | 12.5 | 8 | |
| 3 | 3.1 | 2.7 | >2000 |
| 4 | 2.3 | 3.4 | |
| 5 | 4.7 | 9.5 | |
| 6 | 2.4 | 6 | |
| 7 | — | 7.4 | |
| 8 | 2.2 | 7.2 | |
| 9 | — | 25 | |
| 10 | 2.4 | 5.8 | |
| 11 | 4.2 | 6.2 | |
| 12 | 4.6 | 6 | |
| 13 | 3 | 2 | >2000 |
| 14 | 2 | 3.1 | |
| 15 | 2.2 | 2 | |
| 16 | 1.7 | 1.5 | |
| 17 | 4.8 | 3.6 | |
| 18 | 4 | 4.25 | |
| 19 | 5.5 | 3.5 | |
| 20 | 8.8 | 3.7 | |
| 21 | 2.1 | 3.5 | |
| 22 | — | 3 | |
| 23 | 12 | 12.5 | |
| 24 | 9 | 12.5 | >2000 |
| 25 | 15 | 25 | |
| 26 | 12.5 | 20 | |
| 27 | 25 | 44 | |
| 28 | 32 | 20 | |
| 29 | 45 | 50 | |
| 30 | 4.2 | 4.5 | |
| 31 | 6.5 | 3.6 | |
| 32 | 4.7 | 3.6 | |
| 33 | 9.4 | 4.5 | |
| 34 | 7 | 7.5 | |
| 35 | 19 | 6.5 | |
| 36 | 1.7 | 1.5 | |
| 37 | 1.9 | 2 | |
| 38 | 1.5 | 2 | |
| 39 | 1.75 | 1.6 | |
| 40 | 6.2 | 1.5 | |
| 41 | 6.2 | 4.5 | |
| 42 | 1.25 | 2 | |
| 43 | 15 | 17.5 | |
| 44 | 6.2 | — | |
| 45 | 45 | 50 | |
| 46 | 1.5 | 2 | |
| 47 | 18 | 36 | |
| 48 | 50 | 50 | |
| 49 | 0.5 | 0.4 | 2000 |
| 50 | 17.5 | 15 | |
| 51 | 27 | 50 | |
| 52 | 1.2 | — | >2000 |
| 53 | 5 | 5.8 | |
| 54 | 14 | 12.5 | |
| 55 | 0.6 | 1.1 | |
| 56 | — | 3 | |
| 57 | 7.8 | 9 | |
| 58 | 50 | 8.8 | |
| 59 | 3.4 | 3.1 | |
| 60 | 30 | — | |
| 61 | 0.08 | 0.1 | 1500 |
| 62 | 3.6 | 2.4 | |
| 63 | 9.4 | 16.5 | |
| 64 | — | 4.5 | |
| 65 | 0.28 | 0.75 | |
| 66 | 4.7 | 6 | |
| 67 | 4.4 | 5.6 | |
| 68 | 5 | 6.2 | |
| 69 | 0.5 | 0.2 | |
| 70 | 0.8 | 0.6 | |
| 71 | 1 | 0.8 | |
| 72 | 0.8 | 1 | |
| 73 | 0.6 | 0.8 | |
| 74 | 4 | 6.2 | |
| 75 | 8 | — | |
| 76 | 2.1 | 6.2 | |
| 77 | 2.5 | 6.2 | >2000 |
| 78 | 6.2 | — | |
| 79 | 6.2 | 2 | |
| 80 | 20 | 25 | |
| 81 | 24 | 25 | |
| 82 | 9.6 | 12 | |
| 83 | 12.5 | 6.2 | |
| 84 | 3 | 1.3 | |
| 85 | 3 | 2 | 1000 |
| 86 | 4.5 | 4.8 | |
| 87 | 29 | 44 | |
| 88 | 12.5 | 33 | |
| 89 | 12.5 | 12.5 | |
| 90 | 3 | 8 | |
| 91 | 4.5 | 5.5 | >2000 |
| 92 | 30 | 50 | |
| 93 | 9 | 6 | |
| 94 | 1.5 | 1 | >2000 |
| 95 | 50 | 35 | |
| 96 | 4.7 | 3.6 | |
| 177 | 8 | 15.5 | |
| 97 | 3.9 | 3.2 | |
| 98 | 12.5 | 12.5 | |
| 99 | 50 | 30 | >2000 |
| 111 | 0.28 | — | |
| 100 | 6.2 | — | |
| 101 | 18 | — | |
| 102 | 6.2 | — | |
| 103 | 5 | 6 | |
| 104 | 6.2 | — | |
| 105 | 6.2 | — | |
| 106 | 6.2 | — | |
| 107 | — | 12 | |
| 108 | 5.6 | — | |
| 109 | 0 | 1 | |
| 110 | 0.3 | — | |
| 112 | 0.1 | 0.15 | |
| TOLOXATONE | 60 | 50 | |
| 114 | 3.7 | 2 | >2000 |
| 115 | 3.8 | 4.8 | |
| 116 | 1.6 | 0.95 | |
| 117 | 1.2 | 1.5 | |
| 118 | 1 | 0.1 | >2000 |
| 119 | — | 8 | |
| 120 | — | 3 | |
| 121 | 11 | 8 | |
| 122 | 6.8 | 6.2 | |
| 123 | 2 | 1.4 | >2000 |
| 124 | — | 0.6 | |
| 125 | 5 | 3.5 | |
| 126 | 4.4 | 1.8 | |
| 127 | 5 | 4.3 | |
| 128 | 7.2 | 4.8 | |
| 129 | 7.5 | 12 | |
| 130 | 6.2 | 9.6 | |
| 131 | 12 | 31 | |
| 132 | 3 | 2 | >2000 |
| 133 | 6 | 5.2 | |
| 134 | — | 3.9 | |
| 135 | — | 4.2 | |
| 136 | — | 31 | |
| 137 | — | 6 | |
| 138 | — | 6 | |
| 142 | 18 | 17.5 | |
| 143 | 12.5 | 12 | |
| 144 | 2.2 | 1.1 | |
| 145 | 8.5 | 12 | |
| 146 | 5 | 12.5 | |
| 147 | 1.5 | 2.6 | |
| 148 | 2.2 | — | |
| 149 | 6 | — | |
| 152 | 18 | 15.5 | |
| 153 | 3.8 | 4 | |
| 154 | 19 | 17.5 | |

TABLE VI-continued

| Compound tested Code Number | Test A ED/50/ mg/kg/po | Test B ED/50/ mg/kg/po | Toxicity LD/50 Mouse /mg/kg/po |
|---|---|---|---|
| 155 | 9.6 | 3 | |
| 156 | 0.47 | 0.3 | |
| 157 | 4.7 | 6.2 | |
| 158 | 6 | 6 | |
| 159 | 5.2 | 4.8 | |
| 160 | — | 4.2 | |
| 161 | 1.1 | 0.36 | >2000 |
| 162 | 0.54 | 1.55 | |
| 163 | 1.15 | 8 | |
| 170 | 12.5 | 16 | |
| 171 | 19.5 | 25 | |
| 172 | — | 8.6 | |
| 173 | — | 4.7 | |
| 175 | 5.8 | 9.6 | |
| 176 | 4 | 4 | |
| 150 | 0.7 | 0.5 | |
| 151 | 5.2 | 5 | |
| 164 | 3.4 | 3.4 | |
| 165 | 6.8 | 4.7 | |
| 166 | 3.8 | 3.4 | |
| 167 | 3.7 | 3 | |
| 168 | 25 | 16 | >1000 |
| 169 | 3 | 4.1 | >1000 |
| 174 | 3 | 3.5 | |
| 113 | 3.2 | 3.5 | |
| 178 | 33 | 28 | >1000 |
| 179 | 4.5 | 7 | >1000 |
| 180 | 7.4 | 7.8 | 1000 (20%) |
| 181 | 4 | 9 | >1000 |
| 182 | 3.7 | 5.8 | >1000 |
| 183 | 1.9 | 2.4 | >1000 |
| 184 | 1.2 | 0.72 | >1000 |
| 185 | 12 | 7 | >1000 |
| 186 | 3 | 3 | >1000 |
| 187 | 2.7 | 1.3 | >1000 |
| 188 | 0.3 | 0.4 | — |
| 189 | 2.6 | 0.9 | >1000 |
| 190 | 1 | 0.23 | >1000 |
| 191 | 0.4 | 0.38 | 1000 (40%) |
| 192 | 5.8 | 6 | >1000 |
| 193 | 19 | 30 | — |
| 194 | 6.4 | 5.8 | — |
| 195 | 1.2 | 2.2 | >1000 |
| 196 | — | 0.55 | >1000 |
| 197 | 2.2 | 6.7 | >1000 |
| 198 | 40 | 34 | >1000 |
| 199 | 0.31 | — | >1000 |
| 200 | 1.7 | — | >1000 |
| 201 | 7.4 | 6.8 | >1000 |
| 202 | 10 | 10 | >1000 |
| 203 | 5.2 | 1.4 | 1000 (40%) |
| 204 | 50 | 40 | 1000 (40%) |
| 205 | 10.1 | 3 | >1000 |
| 206 | 6 | 4.3 | >1000 |
| 207 | 9.1 | 7.6 | >1000 |
| 208 | 10 | 4.2 | >1000 |
| 209 | 7 | 6.7 | 1000 (20%) |
| 210 | 26 | 7.4 | >1000 |
| 211 | 2 | 1.2 | 1000 (20%) |
| 212 | 4.3 | 12 | 1000 (40%) |
| 213 | 3 | 2 | 1000 (100%) |
| 214 | 0.84 | 1.8 | 1000 (40%) |
| 215 | 6.2 | 10 | >1000 |
| 216 | 5 | 3 | 1000 (80%) |
| 217 | 1 | 1 | — |
| 218 | 7.2 | 13.5 | >1000 |
| 219 | 7 | 13.5 | >1000 |
| 220 | 50 | 50 | >1000 |
| 234 | 0.6 | 4 | >1000 |

As can be seen from the results shown in Table IV, the compounds of formula (I) have an activity greater than that of the reference compound.

They are indicated in endogenous and exogenous depressive conditions and will be administered orally in the form of tablets, pills or capsules, at a dosage of 50 to 500 mg/day on average, of active substance.

They will also be administered in the form of an injectable solution at the rate of 5–50 mg/day of active substance, the solvent used being formed by binary or ternary mixtures containing for example water, polypropyleneglycol or polyethyleneglycol (quality: 300–400), or any other physiologically acceptable solvent, the relative porportions of the different solvents being adjusted with respect to the dose administered.

I claim:

1. A compound having the formula

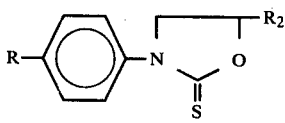

in which $R_2$ is —$CH_2OH$, —$CH_2OR_{16}$ wherein $R_{16}$ is alkyl having from 1 to 3 carbon atoms, or —$CH_2OCOR_{18}$, wherein $R_{18}$ is methyl or ethyl, and when $R_2$ is —$CH_2OH$, R is selected from the group consisting of alkoxy having from 2 to 5 carbon atoms, cyclopentylmethoxy, cyclohexylmethoxy, (cyclohexen-1-yl)methoxy, (tetrahydropyran-4-yl)methoxy, cyanomethoxy, 2-cyanoethoxy, 3-cyanopropoxy, 4-cyanobutoxy,

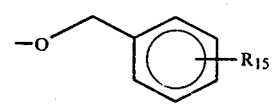

wherein $R_{15}$ is 3—Cl, 4—Cl, 3—F, 4—F, 3—$NO_2$, 3—CN or 3—$CF_3$,

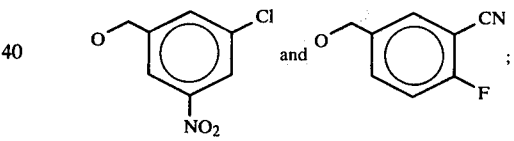

when $R_2$ is —$CH_2OR_{16}$, R is selected form the group consisting of 3-methylbutoxy, cyclopentylmethoxy, cyclohexylmethoxy, 4-cyanobutoxy,

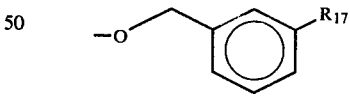

wherein $R_{17}$ is CN or $NO_2$, 3-cyano-5-nitrobenzyloxy or pyridinyl-3-methoxy; and when $R_2$ is —$CH_2OCOR_{18}$, R is cyclohexylmethoxy or

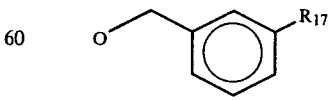

wherein $R_{17}$ is CN or $NO_2$.

2. A compound as claimed in claim 1 in which $R_2$ is —$CH_2OH$.

3. A compound as claimed in claim 1 in which $R_2$ is —$CH_2OR_{16}$.

4. A compound as claimed in claim 1 in which $R_2$ is —$CH_2OCH_3$ and R is

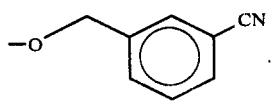

5. A compound as claimed in claim 1 in which $R_2$ is —$CH_2OCH_3$ and R is —O—$(CH_2)_4$—CN.

6. A compound as claimed in claim 1 in which $R_2$ is —$CH_2OCOR_{18}$.

7. A pharmaceutical composition for treating depression comprising a therapeutically effective amount of a compound as claimed in claim 1 and a pharmacologically acceptable carrier.

* * * * *